(12) United States Patent
Zhang

(10) Patent No.: US 9,352,165 B2
(45) Date of Patent: May 31, 2016

(54) METHOD AND APPARATUS FOR VERIFYING DISCRIMINATING OF TACHYCARDIA EVENTS IN A MEDICAL DEVICE HAVING DUAL SENSING VECTORS

(71) Applicant: Medtronic, Inc., Minneapolis, MN (US)

(72) Inventor: Xusheng Zhang, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 19 days.

(21) Appl. No.: 14/255,158

(22) Filed: Apr. 17, 2014

(65) Prior Publication Data

US 2015/0297907 A1  Oct. 22, 2015

(51) Int. Cl.
| A61B 5/04 | (2006.01) |
|---|---|
| A61N 1/38 | (2006.01) |
| A61N 1/39 | (2006.01) |

(52) U.S. Cl.
CPC ............ *A61N 1/3987* (2013.01); *A61N 1/3962* (2013.01)

(58) Field of Classification Search
None
See application file for complete search history.

(56) References Cited

U.S. PATENT DOCUMENTS

| 4,374,382 A | 2/1983 | Markowitz |
|---|---|---|
| 4,556,063 A | 12/1985 | Thompson et al. |
| 4,567,892 A | 2/1986 | Plicchi et al. |
| 4,870,974 A | 10/1989 | Wang |
| 5,127,404 A | 7/1992 | Wyborny et al. |
| 5,176,137 A | 1/1993 | Erickson et al. |
| 5,191,884 A | 3/1993 | Gilli et al. |
| 5,193,535 A | 3/1993 | Bardy et al. |
| 5,257,621 A | 11/1993 | Bardy et al. |
| 5,312,443 A | 5/1994 | Adams et al. |
| 5,330,508 A | 7/1994 | Gunderson |
| 5,334,966 A | 8/1994 | Takeshima et al. |
| 5,447,519 A | 9/1995 | Peterson |
| 5,464,434 A | 11/1995 | Alt |

(Continued)

FOREIGN PATENT DOCUMENTS

| AU | 2010201351 | 4/2010 |
|---|---|---|
| EP | 1631350 | 3/2006 |

(Continued)

OTHER PUBLICATIONS (PCT/US2015/026743) PCT Notification of Transmittal of the International Search Report and the Written Opinion of the International Searching Authority, mailed Jul. 29, 2015, 10 pages.

(Continued)

*Primary Examiner* — Theodore Stigell
*Assistant Examiner* — Natasha Patel

(57) ABSTRACT

A method and medical device for detecting a cardiac event that includes sensing cardiac signals from a plurality of electrodes, the plurality of electrodes forming a first sensing vector sensing a first interval and a second sensing vector simultaneously sensing a second, determining, for each of the first interval and the second interval, whether each beat of the plurality of beats is one of a match beat and a non-match beat, determining whether each beat of the plurality of beats is one of a high confidence beat and a low confidence beat, determining, for each of the first interval and the second interval, the number of beats determined to be both a non-match beat and a high confidence beat is greater than a non-match threshold, and determining whether to deliver therapy for the cardiac event in response to identifying of each of the first interval and the second interval as being one of shockable and not shockable.

21 Claims, 19 Drawing Sheets

(56) References Cited

U.S. PATENT DOCUMENTS

| | | |
|---|---|---|
| 5,545,186 A | 8/1996 | Olson et al. |
| 5,593,431 A | 1/1997 | Sheldon |
| 5,687,733 A | 11/1997 | McKown |
| 5,720,295 A | 2/1998 | Greenhut et al. |
| 5,755,736 A | 5/1998 | Gillberg et al. |
| 5,755,737 A | 5/1998 | Prieve et al. |
| 5,755,739 A | 5/1998 | Sun et al. |
| 5,800,465 A | 9/1998 | Thompson et al. |
| 5,836,975 A | 11/1998 | DeGroot |
| 5,846,263 A | 12/1998 | Peterson et al. |
| 5,855,593 A | 1/1999 | Olson et al. |
| 5,857,977 A | 1/1999 | Caswell et al. |
| 5,893,882 A | 4/1999 | Peterson et al. |
| 5,931,857 A | 8/1999 | Prieve et al. |
| 5,987,356 A | 11/1999 | DeGroot |
| 5,991,656 A | 11/1999 | Olson et al. |
| 6,052,620 A | 4/2000 | Gillberg et al. |
| 6,134,479 A | 10/2000 | Brewer et al. |
| 6,141,581 A | 10/2000 | Olson et al. |
| 6,178,350 B1 | 1/2001 | Olson et al. |
| 6,230,059 B1 | 5/2001 | Duffin |
| 6,236,882 B1 | 5/2001 | Lee et al. |
| 6,259,947 B1 | 7/2001 | Olson et al. |
| 6,287,328 B1 | 9/2001 | Snyder et al. |
| 6,304,773 B1 | 10/2001 | Taylor et al. |
| 6,397,100 B2 | 5/2002 | Stadler et al. |
| 6,449,503 B1 | 9/2002 | Hsu |
| 6,480,734 B1 | 11/2002 | Zhang et al. |
| 6,487,443 B2 | 11/2002 | Olson et al. |
| 6,718,204 B2 | 4/2004 | DeGroot et al. |
| 6,731,978 B2 | 5/2004 | Olson et al. |
| 6,754,527 B2 | 6/2004 | Stroebel et al. |
| 6,754,528 B2 | 6/2004 | Bardy et al. |
| 6,879,856 B2 | 4/2005 | Stadler et al. |
| 6,892,094 B2 | 5/2005 | Ousdigian et al. |
| 6,925,329 B1 | 8/2005 | Sloman |
| 7,010,347 B2 | 3/2006 | Schecter |
| 7,027,858 B2 | 4/2006 | Cao et al. |
| 7,043,299 B2 | 5/2006 | Erlinger et al. |
| 7,065,410 B2 | 6/2006 | Bardy et al. |
| 7,076,289 B2 | 7/2006 | Sarkar et al. |
| 7,103,405 B2 | 9/2006 | Sarkar et al. |
| 7,103,464 B2 | 9/2006 | Zielke |
| 7,130,677 B2 | 10/2006 | Brown et al. |
| 7,149,577 B2 | 12/2006 | Sharma et al. |
| 7,151,962 B2 | 12/2006 | Belk |
| 7,184,831 B2 | 2/2007 | Belk |
| 7,194,302 B2 | 3/2007 | Bardy et al. |
| 7,239,925 B2 | 7/2007 | Bardy et al. |
| 7,248,921 B2 | 7/2007 | Palreddy et al. |
| 7,251,757 B2 | 7/2007 | Ouellette et al. |
| 7,274,962 B2 | 9/2007 | Bardy et al. |
| 7,299,092 B2 | 11/2007 | Bardy et al. |
| 7,299,097 B2 | 11/2007 | Bardy et al. |
| 7,317,942 B2 | 1/2008 | Brown |
| 7,330,757 B2 | 2/2008 | Ostroff et al. |
| 7,376,458 B2 | 5/2008 | Palreddy et al. |
| 7,379,772 B2 | 5/2008 | Bardy et al. |
| 7,392,082 B2 | 6/2008 | Sharma |
| 7,392,085 B2 | 6/2008 | Warren et al. |
| 7,406,350 B2 | 7/2008 | Erlinger et al. |
| 7,444,182 B2 | 10/2008 | Ostroff et al. |
| 7,477,935 B2 | 1/2009 | Palreddy et al. |
| 7,583,579 B2 | 9/2009 | Ueki |
| 7,623,909 B2 | 11/2009 | Sanghera et al. |
| 7,623,913 B2 | 11/2009 | Phillips |
| 7,627,367 B2 | 12/2009 | Warren et al. |
| 7,657,322 B2 | 2/2010 | Bardy et al. |
| 7,728,579 B2 | 6/2010 | Mueller |
| 7,734,333 B2 | 6/2010 | Ghanem et al. |
| 7,734,336 B2 | 6/2010 | Ghanem et al. |
| 7,742,812 B2 | 6/2010 | Ghanem et al. |
| 7,761,142 B2 | 7/2010 | Ghanem et al. |
| 7,761,150 B2 | 7/2010 | Ghanem et al. |
| 7,769,452 B2 | 8/2010 | Ghanem et al. |
| 7,774,049 B2 | 8/2010 | Ghanem et al. |
| 7,774,616 B2 | 8/2010 | Dale et al. |
| 7,783,340 B2 | 8/2010 | Sanghera et al. |
| 7,894,894 B2 | 2/2011 | Stadler et al. |
| 7,904,153 B2 | 3/2011 | Greenhut et al. |
| 7,907,993 B2 | 3/2011 | Ghanem et al. |
| 7,930,024 B2 | 4/2011 | Ousdigian |
| 7,937,135 B2 | 5/2011 | Ghanem et al. |
| 7,941,214 B2 | 5/2011 | Kleckner et al. |
| 7,953,489 B2 | 5/2011 | Warren et al. |
| 7,991,459 B2 | 8/2011 | Palreddy et al. |
| 7,991,471 B2 | 8/2011 | Ghanem et al. |
| 7,996,082 B2 | 8/2011 | Palreddy et al. |
| 8,014,851 B2 | 9/2011 | Ostroff et al. |
| 8,027,720 B2 | 9/2011 | Bardy et al. |
| 8,027,791 B2 | 9/2011 | Soykan |
| 8,050,754 B2 | 11/2011 | Ostroff et al. |
| 8,068,901 B2 | 11/2011 | Ghanem et al. |
| 8,073,532 B2 | 12/2011 | Palreddy et al. |
| 8,095,206 B2 | 1/2012 | Ghanem et al. |
| 8,116,867 B2 | 2/2012 | Ostroff |
| 8,160,684 B2 | 4/2012 | Ghanem et al. |
| 8,160,686 B2 | 4/2012 | Allavatam et al. |
| 8,160,687 B2 | 4/2012 | Warren et al. |
| 8,160,697 B2 | 4/2012 | Warren et al. |
| 8,170,663 B2 | 5/2012 | DeGroot et al. |
| 8,185,198 B2 | 5/2012 | Palreddy et al. |
| 8,200,341 B2 | 6/2012 | Sanghera et al. |
| 8,229,563 B2 | 7/2012 | Warren et al. |
| 8,249,702 B2 | 8/2012 | Warren et al. |
| 8,265,737 B2 | 9/2012 | Warren et al. |
| 8,265,749 B2 | 9/2012 | Allavatam et al. |
| 8,285,375 B2 | 10/2012 | Bardy et al. |
| 8,306,618 B2 | 11/2012 | Ghanem et al. |
| 8,332,022 B2 | 12/2012 | Brown et al. |
| 8,346,357 B2 | 1/2013 | Palreddy et al. |
| 8,364,251 B2 | 1/2013 | Phillips |
| 8,435,185 B2 | 5/2013 | Ghanem et al. |
| 8,437,838 B2 | 5/2013 | Warren et al. |
| 8,457,737 B2 | 6/2013 | Bardy et al. |
| 8,483,813 B2 | 7/2013 | Zhang et al. |
| 8,483,843 B2 | 7/2013 | Sanghera et al. |
| 8,494,630 B2 | 7/2013 | Palreddy et al. |
| 8,548,573 B2 | 10/2013 | Keefe |
| 8,565,878 B2 | 10/2013 | Allavatam et al. |
| 8,588,895 B2 | 11/2013 | Sanghera et al. |
| 8,588,896 B2 | 11/2013 | Allavatam |
| 8,594,775 B2 | 11/2013 | Ghosh et al. |
| 8,594,786 B2 | 11/2013 | Ousdigian |
| 8,600,489 B2 | 12/2013 | Warren et al. |
| 8,611,996 B2 | 12/2013 | Donofrio et al. |
| 8,626,280 B2 | 1/2014 | Allavatam et al. |
| 8,626,285 B2 | 1/2014 | Palreddy et al. |
| 8,700,152 B2 | 4/2014 | Palreddy et al. |
| 8,712,523 B2 | 4/2014 | Sanghera |
| 8,744,555 B2 | 6/2014 | Allavatam et al. |
| 8,750,989 B2 | 6/2014 | Bardy et al. |
| 8,781,567 B2 | 7/2014 | Phillips et al. |
| 8,781,602 B2 | 7/2014 | Sanghera et al. |
| 8,788,023 B2 | 7/2014 | Sanghera et al. |
| 8,825,157 B2 | 9/2014 | Warren et al. |
| 8,983,586 B2 | 3/2015 | Zhang |
| 2002/0058878 A1 | 5/2002 | Kohler et al. |
| 2002/0165459 A1 | 11/2002 | Starobin et al. |
| 2003/0083587 A1 | 5/2003 | Ferek-Petric |
| 2003/0097153 A1 | 5/2003 | Bardy et al. |
| 2003/0120312 A1 | 6/2003 | Cammilli et al. |
| 2004/0021523 A1 | 2/2004 | Sadowy et al. |
| 2004/0030256 A1 | 2/2004 | Lin |
| 2004/0049120 A1 | 3/2004 | Cao et al. |
| 2004/0059237 A1 | 3/2004 | Narayan et al. |
| 2004/0088018 A1 | 5/2004 | Sawchuk et al. |
| 2004/0093037 A1 | 5/2004 | Henry |
| 2004/0111121 A1 | 6/2004 | Brown et al. |
| 2004/0220635 A1 | 11/2004 | Burnes |
| 2004/0254613 A1 | 12/2004 | Ostroff et al. |
| 2005/0038478 A1 | 2/2005 | Klepfer et al. |
| 2006/0025822 A1 | 2/2006 | Zhang |
| 2006/0042809 A1 | 3/2006 | Neufeld et al. |

(56) References Cited

U.S. PATENT DOCUMENTS

| | | |
|---|---|---|
| 2006/0217621 A1 | 9/2006 | Kim et al. |
| 2007/0232948 A1 | 10/2007 | Stadler et al. |
| 2007/0233196 A1 | 10/2007 | Stadler et al. |
| 2007/0233198 A1 | 10/2007 | Ghanem et al. |
| 2007/0239220 A1 | 10/2007 | Greenhut et al. |
| 2007/0270704 A1 | 11/2007 | Ghanem et al. |
| 2007/0276445 A1 | 11/2007 | Sanghera et al. |
| 2007/0276452 A1 | 11/2007 | Sanghera et al. |
| 2008/0103535 A1 | 5/2008 | Ostroff et al. |
| 2008/0132965 A1 | 6/2008 | Ostroff et al. |
| 2008/0269813 A1 | 10/2008 | Greenhut et al. |
| 2008/0275516 A1 | 11/2008 | Ghanem et al. |
| 2008/0288009 A1 | 11/2008 | Kim et al. |
| 2009/0054938 A1 | 2/2009 | Ostroff et al. |
| 2010/0114196 A1 | 5/2010 | Burnes et al. |
| 2010/0331904 A1 | 12/2010 | Warren et al. |
| 2011/0270102 A1 | 11/2011 | Zhang et al. |
| 2011/0270103 A1 | 11/2011 | Zhang et al. |
| 2011/0270107 A1* | 11/2011 | Zhang ............... A61B 5/04525 600/518 |
| 2011/0270110 A1 | 11/2011 | Zhang et al. |
| 2011/0307024 A1 | 12/2011 | Ostroff et al. |
| 2012/0029335 A1 | 2/2012 | Sudam et al. |
| 2012/0095520 A1 | 4/2012 | Zhang et al. |
| 2012/0316612 A1 | 12/2012 | Warren et al. |
| 2013/0030481 A1 | 1/2013 | Ghosh et al. |
| 2013/0109985 A1 | 5/2013 | Gillberg et al. |
| 2013/0197381 A1 | 8/2013 | Charlton et al. |
| 2013/0261471 A1* | 10/2013 | Saha ............... A61B 5/04001 600/484 |
| 2014/0046396 A1 | 2/2014 | Warren et al. |
| 2014/0275917 A1 | 9/2014 | Allavatam et al. |
| 2014/0296932 A1 | 10/2014 | Sanghera et al. |
| 2015/0133954 A1 | 5/2015 | Seifert et al. |

FOREIGN PATENT DOCUMENTS

| | | |
|---|---|---|
| EP | 1631352 | 3/2006 |
| EP | 1659934 | 5/2006 |
| EP | 1774906 | 4/2007 |
| EP | 1803485 | 7/2007 |
| EP | 1803486 | 7/2007 |
| EP | 1827220 | 9/2007 |
| EP | 1827598 | 9/2007 |
| EP | 2025363 | 2/2009 |
| EP | 2029224 | 3/2009 |
| EP | 2029225 | 3/2009 |
| EP | 2029226 | 3/2009 |
| EP | 2077889 | 7/2009 |
| EP | 2114244 | 11/2009 |
| EP | 2166938 A1 | 3/2010 |
| EP | 2268357 | 1/2011 |
| EP | 2268358 | 1/2011 |
| EP | 2313153 | 4/2011 |
| EP | 2446925 | 5/2012 |
| EP | 2446926 | 5/2012 |
| EP | 2455132 | 5/2012 |
| EP | 2459275 | 6/2012 |
| WO | WO 98/05254 A1 | 2/1998 |
| WO | 0047278 | 8/2000 |
| WO | WO 2004/105871 A1 | 12/2004 |
| WO | 2011136916 | 11/2011 |
| WO | 2012075119 A1 | 6/2012 |

OTHER PUBLICATIONS (PCT/US2015/026745) PCT Notification of Transmittal of the International Search Report and the Written Opinion of the International Searching Authority, mailed Aug. 6, 2015, 8 pages.

(PCT/US2015/026954) PCT Notification of Transmittal of the International Search Report and the Written Opinion of the International Searching Authority, mailed Jul. 29, 2015, 11 pages.

(PCT/US2015/032809) PCT Notification of Transmittal of the International Search Report and the Written Opinion of the International Searching Authority, mailed Aug. 6, 2015, 11 pages.

(PCT/US2015/025152) PCT Notification of Transmittal of the International Search Report and the Written Opinion of the International Searching Authority, Mailed Jun. 18, 2015, 9 pages.

(PCT/US2015/026277) PCT Notification of Transmittal of the International Search Report and the Written Opinion of the International Searching Authority, Mailed Jun. 26, 2015, 11 pages.

(PCT/US2015/023351) PCT Notification of Transmittal of the International Search Report and the Written Opinion of the International Searching Authority.

(PCT/US2015/023341) PCT Notification of Transmittal of the International Search Report and the Written Opinion of the International Searching Authority.

(PCT/US2015/023335) PCT Notification of Transmittal of the International Search Report and the Written Opinion of the International Searching Authority.

* cited by examiner

METHOD AND APPARATUS FOR VERIFYING DISCRIMINATING OF TACHYCARDIA EVENTS IN A MEDICAL DEVICE HAVING DUAL SENSING VECTORS

TECHNICAL FIELD

The disclosure relates generally to implantable medical devices and, in particular, to an apparatus and method for discriminating arrhythmias and delivering a therapy in a medical device.

BACKGROUND

Implantable medical devices are available for treating cardiac tachyarrhythmias by delivering anti-tachycardia pacing therapies and electrical shock therapies for cardioverting or defibrillating the heart. Such a device, commonly known as an implantable cardioverter defibrillator or "ICD", senses electrical activity from the heart, determines a patient's heart rate, and classifies the rate according to a number of heart rate zones in order to detect episodes of ventricular tachycardia or fibrillation. Typically a number of rate zones are defined according to programmable detection interval ranges for detecting slow ventricular tachycardia, fast ventricular tachycardia and ventricular fibrillation. Intervals between sensed R-waves, corresponding to the depolarization of the ventricles, are measured. Sensed R-R intervals falling into defined detection interval ranges are counted to provide a count of ventricular tachycardia (VT) or ventricular fibrillation (VF) intervals, for example. A programmable number of intervals to detect (NID) defines the number of tachycardia intervals occurring consecutively or out of a given number of preceding event intervals that are required to detect VT or VF.

Tachyarrhythmia detection may begin with detecting a fast ventricular rate, referred to as rate- or interval-based detection. Once VT or VF is detected based on rate, the morphology of the sensed depolarization signals, e.g. wave shape, amplitude or other features, may be used in discriminating heart rhythms to improve the sensitivity and specificity of tachyarrhythmia detection methods.

A primary goal of a tachycardia detection algorithm is to rapidly respond to a potentially malignant rhythm with a therapy that will terminate the arrhythmia with high certainty. Another goal, however, is to avoid excessive use of ICD battery charge, which shortens the life of the ICD, e.g. due to delivering unnecessary therapies or therapies at a higher voltage than needed to terminate a detected tachyarrhythmia. Minimizing the patient's exposure to painful shock therapies is also an important consideration. Accordingly, a need remains for ICDs that perform tachycardia discrimination with high specificity and control therapy delivery to successfully terminate a detected VT requiring therapy while conserving battery charge and limiting patient exposure to delivered shock therapy by withholding therapy delivery whenever possible in situations where the therapy may not be required.

DETAILED DESCRIPTION

Figure 1:
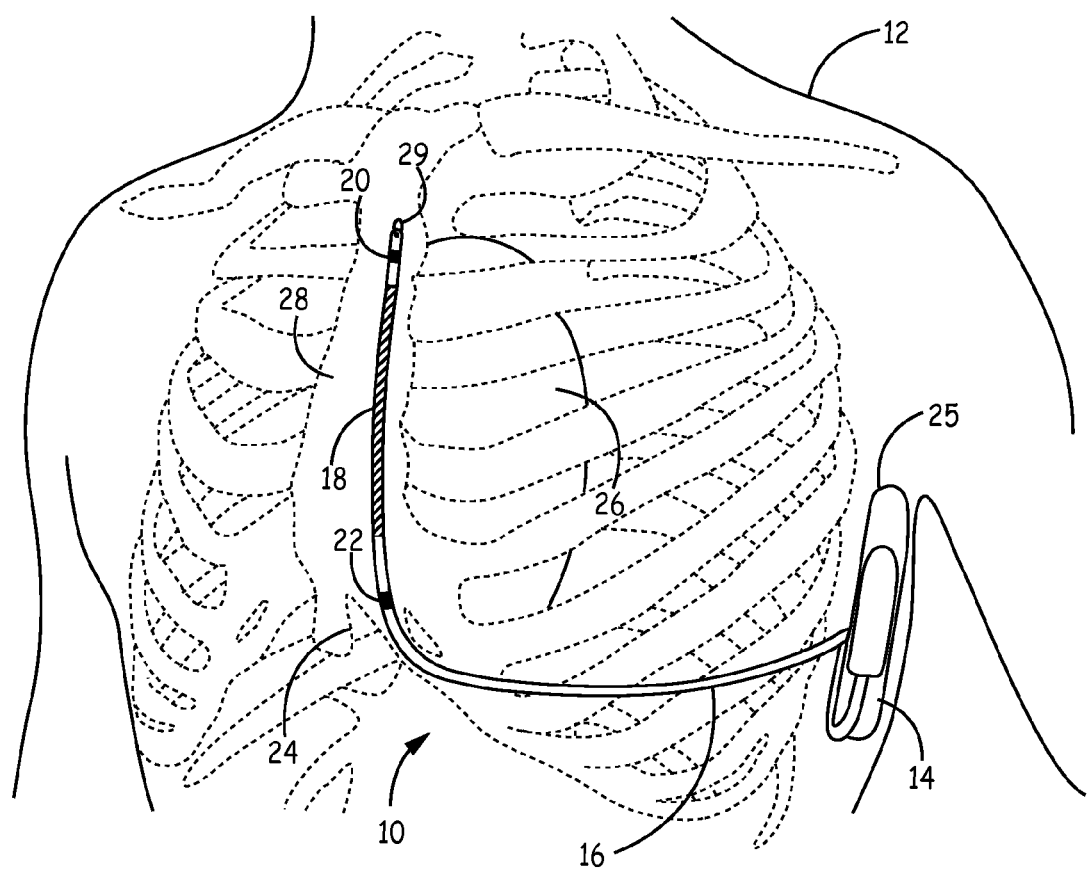
FIG. 1 is a conceptual diagram of a patient implanted with an example extravascular cardiac defibrillation system.

FIG. 1 is a conceptual diagram of a patient 12 implanted with an example extravascular cardiac defibrillation system 10. In the example illustrated in FIG. 1, extravascular cardiac defibrillation system 10 is an implanted subcutaneous ICD system. However, the techniques of this disclosure may also be utilized with other extravascular implanted cardiac defibrillation systems, such as a cardiac defibrillation system having a lead implanted at least partially in a substernal or submuscular location. Additionally, the techniques of this disclosure may also be utilized with other implantable systems, such as implantable pacing systems, implantable neurostimulation systems, drug delivery systems or other systems in which leads, catheters or other components are implanted at extravascular locations within patient 12. This disclosure, however, is described in the context of an implantable extravascular cardiac defibrillation system for purposes of illustration.

Extravascular cardiac defibrillation system 10 includes an implantable cardioverter defibrillator (ICD) 14 connected to at least one implantable cardiac defibrillation lead 16. ICD 14 of FIG. 1 is implanted subcutaneously on the left side of patient 12. Defibrillation lead 16, which is connected to ICD 14, extends medially from ICD 14 toward sternum 28 and xiphoid process 24 of patient 12. At a location near xiphoid process 24, defibrillation lead 16 bends or turns and extends subcutaneously superior, substantially parallel to sternum 28. In the example illustrated in FIG. 1, defibrillation lead 16 is implanted such that lead 16 is offset laterally to the left side of the body of sternum 28 (i.e., towards the left side of patient 12).

Defibrillation lead 16 is placed along sternum 28 such that a therapy vector between defibrillation electrode 18 and a second electrode (such as a housing or can 25 of ICD 14 or an electrode placed on a second lead) is substantially across the ventricle of heart 26. The therapy vector may, in one example, be viewed as a line that extends from a point on the defibrillation electrode 18 to a point on the housing or can 25 of ICD 14. In another example, defibrillation lead 16 may be placed along sternum 28 such that a therapy vector between defibrillation electrode 18 and the housing or can 25 of ICD 14 (or other electrode) is substantially across an atrium of heart 26. In this case, extravascular ICD system 10 may be used to provide atrial therapies, such as therapies to treat atrial fibrillation.

The embodiment illustrated in FIG. 1 is an example configuration of an extravascular ICD system 10 and should not be considered limiting of the techniques described herein. For example, although illustrated as being offset laterally from the midline of sternum 28 in the example of FIG. 1, defibrillation lead 16 may be implanted such that lead 16 is offset to the right of sternum 28 or more centrally located over sternum 28. Additionally, defibrillation lead 16 may be implanted such that it is not substantially parallel to sternum 28, but instead offset from sternum 28 at an angle (e.g., angled lateral from sternum 28 at either the proximal or distal end). As another example, the distal end of defibrillation lead 16 may be positioned near the second or third rib of patient 12. However, the distal end of defibrillation lead 16 may be positioned further superior or inferior depending on the location of ICD 14, location of electrodes 18, 20, and 22, or other factors.

Although ICD 14 is illustrated as being implanted near a midaxillary line of patient 12, ICD 14 may also be implanted at other subcutaneous locations on patient 12, such as further posterior on the torso toward the posterior axillary line, further anterior on the torso toward the anterior axillary line, in a pectoral region, or at other locations of patient 12. In instances in which ICD 14 is implanted pectorally, lead 16 would follow a different path, e.g., across the upper chest area and inferior along sternum 28. When the ICD 14 is implanted in the pectoral region, the extravascular ICD system may include a second lead including a defibrillation electrode that extends along the left side of the patient such that the defibrillation electrode of the second lead is located along the left side of the patient to function as an anode or cathode of the therapy vector of such an ICD system.

ICD 14 includes a housing or can 25 that forms a hermetic seal that protects components within ICD 14. The housing 25 of ICD 14 may be formed of a conductive material, such as titanium or other biocompatible conductive material or a combination of conductive and non-conductive materials. In some instances, the housing 25 of ICD 14 functions as an electrode (referred to as a housing electrode or can electrode) that is used in combination with one of electrodes 18, 20, or 22 to deliver a therapy to heart 26 or to sense electrical activity of heart 26. ICD 14 may also include a connector assembly (sometimes referred to as a connector block or header) that includes electrical feedthroughs through which electrical connections are made between conductors within defibrillation lead 16 and electronic components included within the housing. Housing may enclose one or more components, including processors, memories, transmitters, receivers, sensors, sensing circuitry, therapy circuitry and other appropriate components (often referred to herein as modules).

Defibrillation lead 16 includes a lead body having a proximal end that includes a connector configured to connect to ICD 14 and a distal end that includes one or more electrodes 18, 20, and 22. The lead body of defibrillation lead 16 may be formed from a non-conductive material, including silicone, polyurethane, fluoropolymers, mixtures thereof, and other appropriate materials, and shaped to form one or more lumens within which the one or more conductors extend. However, the techniques are not limited to such constructions. Although defibrillation lead 16 is illustrated as including three electrodes 18, 20 and 22, defibrillation lead 16 may include more or fewer electrodes.

Defibrillation lead 16 includes one or more elongated electrical conductors (not illustrated) that extend within the lead body from the connector on the proximal end of defibrillation lead 16 to electrodes 18, 20 and 22. In other words, each of the one or more elongated electrical conductors contained within the lead body of defibrillation lead 16 may engage with respective ones of electrodes 18, 20 and 22. When the connector at the proximal end of defibrillation lead 16 is connected to ICD 14, the respective conductors may electrically couple to circuitry, such as a therapy module or a sensing module, of ICD 14 via connections in connector assembly, including associated feedthroughs. The electrical conductors transmit therapy from a therapy module within ICD 14 to one or more of electrodes 18, 20 and 22 and transmit sensed electrical signals from one or more of electrodes 18, 20 and 22 to the sensing module within ICD 14.

ICD 14 may sense electrical activity of heart 26 via one or more sensing vectors that include combinations of electrodes 20 and 22 and the housing or can 25 of ICD 14. For example, ICD 14 may obtain electrical signals sensed using a sensing vector between electrodes 20 and 22, obtain electrical signals sensed using a sensing vector between electrode 20 and the conductive housing or can 25 of ICD 14, obtain electrical signals sensed using a sensing vector between electrode 22 and the conductive housing or can 25 of ICD 14, or a combination thereof. In some instances, ICD 14 may sense cardiac electrical signals using a sensing vector that includes defibrillation electrode 18, such as a sensing vector between defibrillation electrode 18 and one of electrodes 20 or 22, or a sensing vector between defibrillation electrode 18 and the housing or can 25 of ICD 14.

ICD may analyze the sensed electrical signals to detect tachycardia, such as ventricular tachycardia or ventricular fibrillation, and in response to detecting tachycardia may generate and deliver an electrical therapy to heart 26. For example, ICD 14 may deliver one or more defibrillation shocks via a therapy vector that includes defibrillation electrode 18 of defibrillation lead 16 and the housing or can 25. Defibrillation electrode 18 may, for example, be an elongated coil electrode or other type of electrode. In some instances, ICD 14 may deliver one or more pacing therapies prior to or after delivery of the defibrillation shock, such as anti-tachycardia pacing (ATP) or post shock pacing. In these instances, ICD 14 may generate and deliver pacing pulses via therapy vectors that include one or both of electrodes 20 and 22 and/or the housing or can 25. Electrodes 20 and 22 may comprise ring electrodes, hemispherical electrodes, coil electrodes, helix electrodes, segmented electrodes, directional electrodes, or other types of electrodes, or combination thereof. Electrodes 20 and 22 may be the same type of electrodes or different types of electrodes, although in the example of FIG. 1 both electrodes 20 and 22 are illustrated as ring electrodes.

Defibrillation lead 16 may also include an attachment feature 29 at or toward the distal end of lead 16. The attachment feature 29 may be a loop, link, or other attachment feature. For example, attachment feature 29 may be a loop formed by a suture. As another example, attachment feature 29 may be a loop, link, ring of metal, coated metal or a polymer. The attachment feature 29 may be formed into any of a number of shapes with uniform or varying thickness and varying dimensions. Attachment feature 29 may be integral to the lead or may be added by the user prior to implantation. Attachment feature 29 may be useful to aid in implantation of lead 16 and/or for securing lead 16 to a desired implant location. In some instances, defibrillation lead 16 may include a fixation mechanism in addition to or instead of the attachment feature. Although defibrillation lead 16 is illustrated with an attachment feature 29, in other examples lead 16 may not include an attachment feature 29.

Lead 16 may also include a connector at the proximal end of lead 16, such as a DF4 connector, bifurcated connector (e.g., DF-1/IS-1 connector), or other type of connector. The connector at the proximal end of lead 16 may include a terminal pin that couples to a port within the connector assembly of ICD 14. In some instances, lead 16 may include an attachment feature at the proximal end of lead 16 that may be coupled to an implant tool to aid in implantation of lead 16. The attachment feature at the proximal end of the lead may separate from the connector and may be either integral to the lead or added by the user prior to implantation.

Defibrillation lead 16 may also include a suture sleeve or other fixation mechanism (not shown) located proximal to electrode 22 that is configured to fixate lead 16 near the xiphoid process or lower sternum location. The fixation mechanism (e.g., suture sleeve or other mechanism) may be integral to the lead or may be added by the user prior to implantation.

The example illustrated in FIG. 1 is exemplary in nature and should not be considered limiting of the techniques described in this disclosure. For instance, extravascular cardiac defibrillation system 10 may include more than one lead. In one example, extravascular cardiac defibrillation system 10 may include a pacing lead in addition to defibrillation lead 16.

In the example illustrated in FIG. 1, defibrillation lead 16 is implanted subcutaneously, e.g., between the skin and the ribs or sternum. In other instances, defibrillation lead 16 (and/or the optional pacing lead) may be implanted at other extravascular locations. In one example, defibrillation lead 16 may be implanted at least partially in a substernal location. In such a configuration, at least a portion of defibrillation lead 16 may be placed under or below the sternum in the mediastinum and, more particularly, in the anterior mediastinum. The anterior mediastinum is bounded laterally by pleurae, posteriorly by pericardium, and anteriorly by sternum 28. Defibrillation lead 16 may be at least partially implanted in other extra-pericardial locations, i.e., locations in the region around, but not in direct contact with, the outer surface of heart 26. These other extra-pericardial locations may include in the mediastinum but offset from sternum 28, in the superior mediastinum, in the middle mediastinum, in the posterior mediastinum, in the sub-xiphoid or inferior xiphoid area, near the apex of the heart, or other location not in direct contact with heart 26 and not subcutaneous. In still further instances, the lead may be implanted at a pericardial or epicardial location outside of the heart 26.

Figure 2:
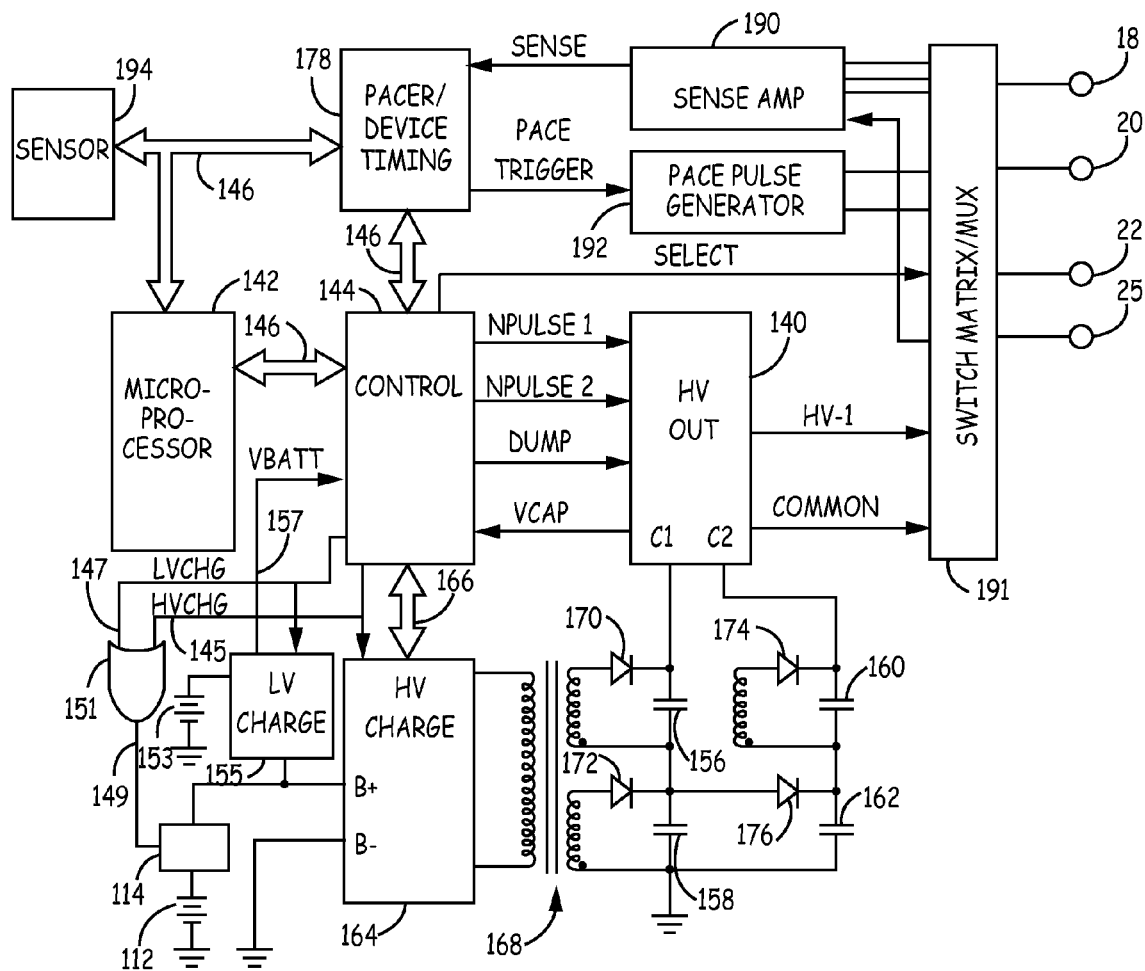
FIG. 2 is an exemplary schematic diagram of electronic circuitry within a hermetically sealed housing of a subcutaneous device according to an embodiment of the present invention.

FIG. 2 is an exemplary schematic diagram of electronic circuitry within a hermetically sealed housing of a subcutaneous device according to an embodiment of the present invention. As illustrated in FIG. 2, subcutaneous device 14 includes a low voltage battery 153 coupled to a power supply (not shown) that supplies power to the circuitry of the subcutaneous device 14 and the pacing output capacitors to supply pacing energy in a manner well known in the art. The low voltage battery 153 may be formed of one or two conventional $LiCF_x$, $LiMnO_2$ or $LiI_2$ cells, for example. The subcutaneous device 14 also includes a high voltage battery 112 that may be formed of one or two conventional LiSVO or $LiMnO_2$ cells. Although two both low voltage battery and a high voltage battery are shown in FIG. 2, according to an embodiment of the present invention, the device 14 could utilize a single battery for both high and low voltage uses.

Further referring to FIG. 2, subcutaneous device 14 functions are controlled by means of software, firmware and hardware that cooperatively monitor the ECG signal, determine when a cardioversion-defibrillation shock or pacing is necessary, and deliver prescribed cardioversion-defibrillation and pacing therapies. The subcutaneous device 14 may incorporate circuitry set forth in commonly assigned U.S. Pat. No. 5,163,427 "Apparatus for Delivering Single and Multiple Cardioversion and Defibrillation Pulses" to Keimel and U.S. Pat. No. 5,188,105 "Apparatus and Method for Treating a Tachyarrhythmia" to Keimel for selectively delivering single phase, simultaneous biphasic and sequential biphasic cardioversion-defibrillation shocks typically employing ICD IPG housing electrodes 28 coupled to the COMMON output 123 of high voltage output circuit 140 and cardioversion-defibrillation electrode 24 disposed posteriorly and subcutaneously and coupled to the HV1 output 113 of the high voltage output circuit 140.

The cardioversion-defibrillation shock energy and capacitor charge voltages can be intermediate to those supplied by ICDs having at least one cardioversion-defibrillation electrode in contact with the heart and most AEDs having cardioversion-defibrillation electrodes in contact with the skin. The typical maximum voltage necessary for ICDs using most biphasic waveforms is approximately 750 Volts with an associated maximum energy of approximately 40 Joules. The typical maximum voltage necessary for AEDs is approximately 2000-5000 Volts with an associated maximum energy of approximately 200-360 Joules depending upon the model and waveform used. The subcutaneous device 14 of the present invention uses maximum voltages in the range of about 300 to approximately 1000 Volts and is associated with energies of approximately 25 to 150 joules or more. The total high voltage capacitance could range from about 50 to about 300 microfarads. Such cardioversion-defibrillation shocks are only delivered when a malignant tachyarrhythmia, e.g., ventricular fibrillation is detected through processing of the far field cardiac ECG employing the detection algorithms as described herein below.

In FIG. 2, sense amp 190 in conjunction with pacer/device timing circuit 178 processes the far field ECG sense signal that is developed across a particular ECG sense vector defined by a selected pair of the subcutaneous electrodes 18, 20, 22 and the can or housing 25 of the device 14, or, optionally, a virtual signal (i.e., a mathematical combination of two vectors) if selected. The selection of the sensing electrode pair is made through the switch matrix/MUX 191 in a manner to provide the most reliable sensing of the ECG signal of interest, which would be the R wave for patients who are believed to be at risk of ventricular fibrillation leading to sudden death. The far field ECG signals are passed through the switch matrix/MUX 191 to the input of the sense amplifier 190 that, in conjunction with pacer/device timing circuit 178, evaluates the sensed EGM. Bradycardia, or asystole, is typically determined by an escape interval timer within the pacer timing circuit 178 and/or the control circuit 144. Pace Trigger signals are applied to the pacing pulse generator 192 generating pacing stimulation when the interval between successive R-waves exceeds the escape interval. Bradycardia pacing is often temporarily provided to maintain cardiac output after delivery of a cardioversion-defibrillation shock that may cause the heart to slowly beat as it recovers back to normal function. Sensing subcutaneous far field signals in the presence of noise may be aided by the use of appropriate denial and extensible accommodation periods as described in U.S. Pat. No. 6,236,882 "Noise Rejection for Monitoring ECGs" to Lee, et al and incorporated herein by reference in its' entirety.

Detection of a malignant tachyarrhythmia is determined in the Control circuit 144 as a function of the intervals between R-wave sense event signals that are output from the pacer/device timing 178 and sense amplifier circuit 190 to the timing and control circuit 144. It should be noted that the present invention utilizes not only interval based signal analysis method but also supplemental sensors and morphology processing method and apparatus as described herein below.

Supplemental sensors such as tissue color, tissue oxygenation, respiration, patient activity and the like may be used to contribute to the decision to apply or withhold a defibrillation therapy as described generally in U.S. Pat. No. 5,464,434 "Medical Interventional Device Responsive to Sudden Hemodynamic Change" to Alt and incorporated herein by reference in its entirety. Sensor processing block 194 provides sensor data to microprocessor 142 via data bus 146. Specifically, patient activity and/or posture may be determined by the apparatus and method as described in U.S. Pat. No. 5,593,431 "Medical Service Employing Multiple DC Accelerometers for Patient Activity and Posture Sensing and Method" to Sheldon and incorporated herein by reference in its entirety. Patient respiration may be determined by the apparatus and method as described in U.S. Pat. No. 4,567,892 "Implantable Cardiac Pacemaker" to Plicchi, et al and incorporated herein by reference in its entirety. Patient tissue oxygenation or tissue color may be determined by the sensor apparatus and method as described in U.S. Pat. No. 5,176,137 to Erickson, et al and incorporated herein by reference in its entirety. The oxygen sensor of the '137 patent may be located in the subcutaneous device pocket or, alternatively, located on the lead 18 to enable the sensing of contacting or near-contacting tissue oxygenation or color.

Certain steps in the performance of the detection algorithm criteria are cooperatively performed in microcomputer 142, including microprocessor, RAM and ROM, associated circuitry, and stored detection criteria that may be programmed into RAM via a telemetry interface (not shown) conventional in the art. Data and commands are exchanged between microcomputer 142 and timing and control circuit 144, pacer timing/amplifier circuit 178, and high voltage output circuit 140 via a bi-directional data/control bus 146. The pacer timing/amplifier circuit 178 and the control circuit 144 are clocked at a slow clock rate. The microcomputer 142 is normally asleep, but is awakened and operated by a fast clock by interrupts developed by each R-wave sense event, on receipt of a downlink telemetry programming instruction or upon delivery of cardiac pacing pulses to perform any necessary mathematical calculations, to perform tachycardia and fibrillation detection procedures, and to update the time intervals monitored and controlled by the timers in pacer/device timing circuitry 178.

When a malignant tachycardia is detected, high voltage capacitors 156, 158, 160, and 162 are charged to a pre-programmed voltage level by a high-voltage charging circuit 164. It is generally considered inefficient to maintain a constant charge on the high voltage output capacitors 156, 158, 160, 162. Instead, charging is initiated when control circuit 144 issues a high voltage charge command HVCHG delivered on line 145 to high voltage charge circuit 164 and charging is controlled by means of bi-directional control/data bus 166 and a feedback signal VCAP from the HV output circuit 140. High voltage output capacitors 156, 158, 160 and 162 may be of film, aluminum electrolytic or wet tantalum construction.

The negative terminal of high voltage battery 112 is directly coupled to system ground. Switch circuit 114 is normally open so that the positive terminal of high voltage battery 112 is disconnected from the positive power input of the high voltage charge circuit 164. The high voltage charge command HVCHG is also conducted via conductor 149 to the control input of switch circuit 114, and switch circuit 114 closes in response to connect positive high voltage battery voltage EXT B+ to the positive power input of high voltage charge circuit 164. Switch circuit 114 may be, for example, a field effect transistor (FET) with its source-to-drain path interrupting the EXT B+ conductor 118 and its gate receiving the HVCHG signal on conductor 145. High voltage charge circuit 164 is thereby rendered ready to begin charging the high voltage output capacitors 156, 158, 160, and 162 with charging current from high voltage battery 112.

High voltage output capacitors 156, 158, 160, and 162 may be charged to very high voltages, e.g., 300-1000V, to be discharged through the body and heart between the electrode pair of subcutaneous cardioversion-defibrillation electrodes 113 and 123. The details of the voltage charging circuitry are also not deemed to be critical with regard to practicing the present invention; one high voltage charging circuit believed to be suitable for the purposes of the present invention is disclosed. High voltage capacitors 156, 158, 160 and 162 may be charged, for example, by high voltage charge circuit 164 and a high frequency, high-voltage transformer 168 as described in detail in commonly assigned U.S. Pat. No. 4,548,209 "Energy Converter for Implantable Cardioverter" to Wielders, et al. Proper charging polarities are maintained by diodes 170, 172, 174 and 176 interconnecting the output windings of high-voltage transformer 168 and the capacitors 156, 158, 160, and 162. As noted above, the state of capacitor charge is monitored by circuitry within the high voltage output circuit 140 that provides a VCAP, feedback signal indicative of the voltage to the timing and control circuit 144. Timing and control circuit 144 terminates the high voltage charge command HVCHG when the VCAP signal matches the programmed capacitor output voltage, i.e., the cardioversion-defibrillation peak shock voltage.

Control circuit 144 then develops first and second control signals NPULSE 1 and NPULSE 2, respectively, that are applied to the high voltage output circuit 140 for triggering the delivery of cardioverting or defibrillating shocks. In particular, the NPULSE 1 signal triggers discharge of the first capacitor bank, comprising capacitors 156 and 158. The NPULSE 2 signal triggers discharge of the first capacitor bank and a second capacitor bank, comprising capacitors 160 and 162. It is possible to select between a plurality of output pulse regimes simply by modifying the number and time order of assertion of the NPULSE 1 and NPULSE 2 signals. The NPULSE 1 signals and NPULSE 2 signals may be provided sequentially, simultaneously or individually. In this way, control circuitry 144 serves to control operation of the high voltage output stage 140, which delivers high energy cardioversion-defibrillation shocks between the pair of the cardioversion-defibrillation electrodes 18 and 25 coupled to the HV-1 and COMMON output as shown in FIG. 2.

Thus, subcutaneous device 14 monitors the patient's cardiac status and initiates the delivery of a cardioversion-defibrillation shock through the cardioversion-defibrillation electrodes 18 and 25 in response to detection of a tachyarrhythmia requiring cardioversion-defibrillation. The high HVCHG signal causes the high voltage battery 112 to be connected through the switch circuit 114 with the high voltage charge circuit 164 and the charging of output capacitors 156, 158, 160, and 162 to commence. Charging continues until the programmed charge voltage is reflected by the VCAP signal, at which point control and timing circuit 144 sets the HVCHG signal low terminating charging and opening switch circuit 114. The subcutaneous device 14 can be programmed to attempt to deliver cardioversion shocks to the heart in the manners described above in timed synchrony with a detected R-wave or can be programmed or fabricated to deliver defibrillation shocks to the heart in the manners described above without attempting to synchronize the delivery to a detected R-wave. Episode data related to the detection of the tachyarrhythmia and delivery of the cardioversion-defibrillation shock can be stored in RAM for uplink telemetry transmission to an external programmer as is well known in the art to facilitate in diagnosis of the patient's cardiac state. A patient receiving the device 14 on a prophylactic basis would be instructed to report each such episode to the attending physician for further evaluation of the patient's condition and assessment for the need for implantation of a more sophisticated ICD.

Subcutaneous device 14 desirably includes telemetry circuit (not shown in FIG. 2), so that it is capable of being programmed by means of external programmer 20 via a 2-way telemetry link (not shown). Uplink telemetry allows device status and diagnostic/event data to be sent to external programmer 20 for review by the patient's physician. Downlink telemetry allows the external programmer via physician control to allow the programming of device function and the optimization of the detection and therapy for a specific patient. Programmers and telemetry systems suitable for use in the practice of the present invention have been well known for many years. Known programmers typically communicate with an implanted device via a bi-directional radio-frequency telemetry link, so that the programmer can transmit control commands and operational parameter values to be received by the implanted device, so that the implanted device can communicate diagnostic and operational data to the programmer. Programmers believed to be suitable for the purposes of practicing the present invention include the Models 9790 and CareLink® programmers, commercially available from Medtronic, Inc., Minneapolis, Minn.

Various telemetry systems for providing the necessary communications channels between an external programming unit and an implanted device have been developed and are well known in the art. Telemetry systems believed to be suitable for the purposes of practicing the present invention are disclosed, for example, in the following U.S. patents: U.S. Pat. No. 5,127,404 to Wyborny et al. entitled "Telemetry Format for Implanted Medical Device"; U.S. Pat. No. 4,374,382 to Markowitz entitled "Marker Channel Telemetry System for a Medical Device"; and U.S. Pat. No. 4,556,063 to Thompson et al. entitled "Telemetry System for a Medical Device". The Wyborny et al. '404, Markowitz '382, and Thompson et al. '063 patents are commonly assigned to the assignee of the present invention, and are each hereby incorporated by reference herein in their respective entireties.

According to an embodiment of the present invention, in order to automatically select the preferred ECG vector set, it is necessary to have an index of merit upon which to rate the quality of the signal. "Quality" is defined as the signal's ability to provide accurate heart rate estimation and accurate morphological waveform separation between the patient's usual sinus rhythm and the patient's ventricular tachyarrhythmia.

Appropriate indices may include R-wave amplitude, R-wave peak amplitude to waveform amplitude between R-waves (i.e., signal to noise ratio), low slope content, relative high versus low frequency power, mean frequency estimation, probability density function, or some combination of these metrics.

Automatic vector selection might be done at implantation or periodically (daily, weekly, monthly) or both. At implant, automatic vector selection may be initiated as part of an automatic device turn-on procedure that performs such activities as measure lead impedances and battery voltages. The device turn-on procedure may be initiated by the implanting physician (e.g., by pressing a programmer button) or, alternatively, may be initiated automatically upon automatic detection of device/lead implantation. The turn-on procedure may also use the automatic vector selection criteria to determine if ECG vector quality is adequate for the current patient and for the device and lead position, prior to suturing the subcutaneous device 14 device in place and closing the incision. Such an ECG quality indicator would allow the implanting physician to maneuver the device to a new location or orientation to improve the quality of the ECG signals as required. The preferred ECG vector or vectors may also be selected at implant as part of the device turn-on procedure. The preferred vectors might be those vectors with the indices that maximize rate estimation and detection accuracy. There may also be an a priori set of vectors that are preferred by the physician, and as long as those vectors exceed some minimum threshold, or are only slightly worse than some other more desirable vectors, the a priori preferred vectors are chosen. Certain vectors may be considered nearly identical such that they are not tested unless the a priori selected vector index falls below some predetermined threshold.

Depending upon metric power consumption and power requirements of the device, the ECG signal quality metric may be measured on the range of vectors (or alternatively, a subset) as often as desired. Data may be gathered, for example, on a minute, hourly, daily, weekly or monthly basis. More frequent measurements (e.g., every minute) may be averaged over time and used to select vectors based upon susceptibility of vectors to occasional noise, motion noise, or EMI, for example.

Alternatively, the subcutaneous device 14 may have an indicator/sensor of patient activity (piezo-resistive, accelerometer, impedance, or the like) and delay automatic vector measurement during periods of moderate or high patient activity to periods of minimal to no activity. One representative scenario may include testing/evaluating ECG vectors once daily or weekly while the patient has been determined to be asleep (using an internal clock (e.g., 2:00 am) or, alternatively, infer sleep by determining the patient's position (via a 2- or 3-axis accelerometer) and a lack of activity).

If infrequent automatic, periodic measurements are made, it may also be desirable to measure noise (e.g., muscle, motion, EMI, etc.) in the signal and postpone the vector selection measurement when the noise has subsided.

Subcutaneous device 14 may optionally have an indicator of the patient's posture (via a 2- or 3-axis accelerometer). This sensor may be used to ensure that the differences in ECG quality are not simply a result of changing posture/position. The sensor may be used to gather data in a number of postures so that ECG quality may be averaged over these postures or, alternatively, selected for a preferred posture.

In the preferred embodiment, vector quality metric calculations would occur a number of times over approximately 1 minute, once per day, for each vector. These values would be averaged for each vector over the course of one week. Averaging may consist of a moving average or recursive average depending on time weighting and memory considerations. In this example, the preferred vector(s) would be selected once per week.

Figure 3:
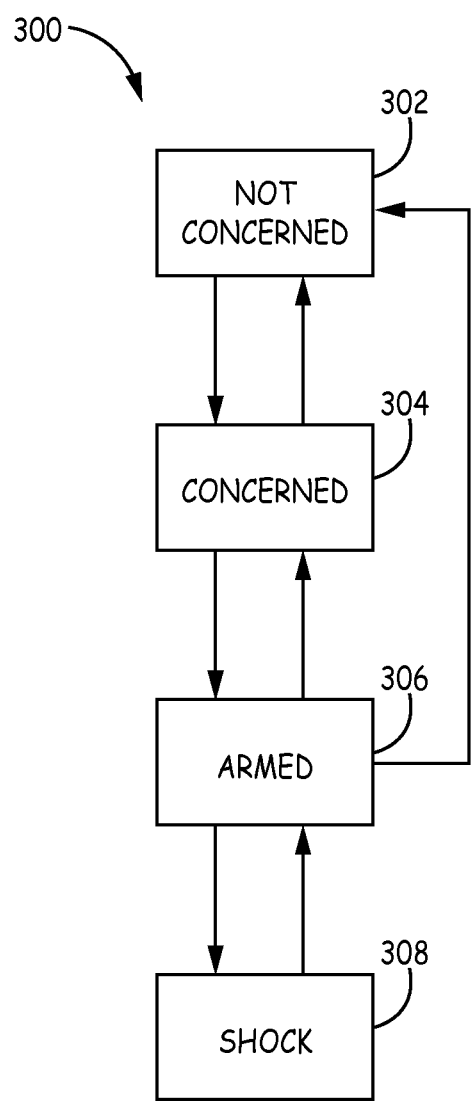
FIG. 3 is a state diagram of detection of arrhythmias in a medical device according to an embodiment of the present invention.

FIG. 3 is a state diagram of detection of arrhythmias in a medical device according to an embodiment of the present invention. As illustrated in FIG. 3, during normal operation, the device 14 is in a not concerned state 302, during which R-wave intervals are being evaluated to identify periods of rapid rates and/or the presence of asystole. Upon detection of short R-wave intervals simultaneously in two separate ECG sensing vectors, indicative of an event that, if confirmed, may require the delivery of therapy, the device 14 transitions from the not concerned state 302 to a concerned state 304. In the concerned state 304 the device 14 evaluates a predetermined window of ECG signals to determine the likelihood that the signal is corrupted with noise and to discriminate rhythms requiring shock therapy from those that do not require shock therapy, using a combination of R-wave intervals and ECG signal morphology information.

If a rhythm requiring shock therapy continues to be detected while in the concerned state 304, the device 14 transitions from the concerned state 304 to an armed state 306. If a rhythm requiring shock therapy is no longer detected while the device is in the concerned state 304 and the R-wave intervals are determined to no longer be short, the device 14 returns to the not concerned state 302. However, if a rhythm requiring shock therapy is no longer detected while the device is in the concerned state 304, but the R-wave intervals continue to be detected as being short, processing continues in the concerned state 304.

In the armed state 306, the device 14 charges the high voltage shocking capacitors and continues to monitor R-wave intervals and ECG signal morphology for spontaneous termination. If spontaneous termination of the rhythm requiring shock therapy occurs, the device 14 returns to the not concerned state 302. If the rhythm requiring shock therapy is still determined to be occurring once the charging of the capacitors is completed, the device 14 transitions from the armed state 306 to a shock state 308. In the shock state 308, the device 14 delivers a shock and returns to the armed state 306 to evaluate the success of the therapy delivered.

The transitioning between the not concerned state 302, the concerned state 304, the armed state 306 and the shock state 308 may be performed as described in detail in U.S. Pat. No. 7,894,894 to Stadler et al., incorporated herein by reference in it's entirety.

Figure 4:
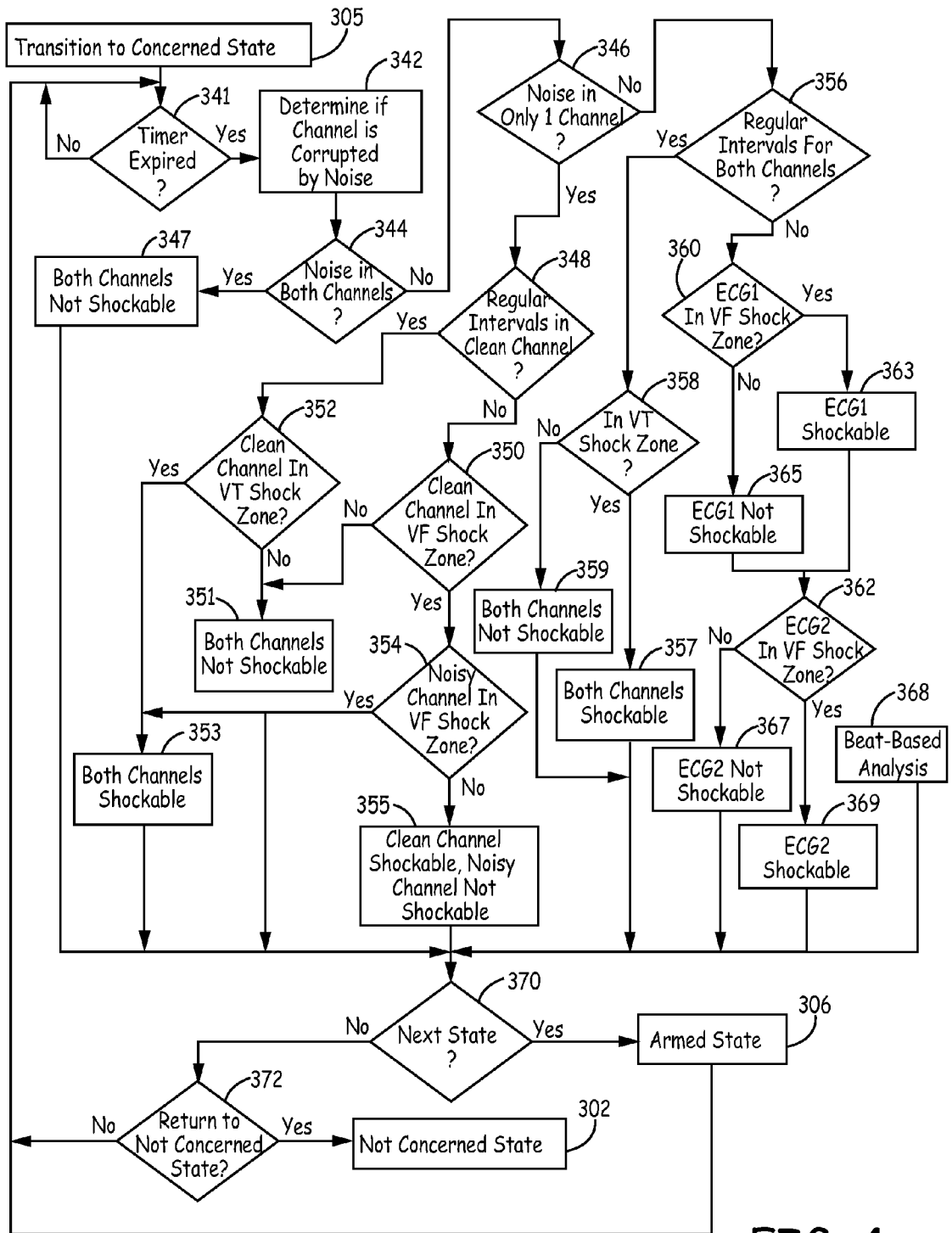
FIG. 4 is a flowchart of a method for detecting arrhythmias in a subcutaneous device according to an embodiment of the present disclosure.

FIG. 4 is a flowchart of a method for detecting arrhythmias in a subcutaneous device according to an embodiment of the present disclosure. As illustrated in FIG. 4, device 14 continuously evaluates the two channels ECG1 and ECG2 associated with two predetermined electrode vectors to determine when sensed events occur. For example, the electrode vectors for the two channels ECG1 and ECG2 may include a first vector (ECG1) selected between electrode 20 positioned on lead 16 and the housing or can 25 of ICD 14, while the other electrode vector (ECG 2) is a vertical electrode vector between electrode 20 and electrode 22 positioned along the lead 16. However, the two sensing channels may in any combination of possible vectors, including those formed by the electrodes shown in FIG. 2, or other additional electrodes (not shown) that may be included along the lead or positioned along the housing of ICD 14.

According to an embodiment of the present application, for example, the device 14 determines whether to transition from the not concerned state 302 to the concerned state 304 by determining a heart rate estimate in response to the sensing of R-waves, as described in U.S. Pat. No. 7,894,894 to Stadler et al., incorporated herein by reference in it's entirety.

Upon transition from the not concerned state to the concerned state, Block 305, a most recent window of ECG data from both channels ECG1 and ECG2 are utilized, such as three seconds, for example, so that processing is triggered in the concerned state 304 by a three-second timeout, rather than by the sensing of an R-wave, which is utilized when in the not concerned state 302. It is understood that while the processing is described as being triggered over a three second period, other times periods for the processing time utilized when in the concerned state 304 may be chosen, but should preferably be within a range of 0.5 to 10 seconds. As a result, although sensing of individual R-waves continues to occur in both channels ECG1 and ECG2 when in the concerned state 304, and the buffer of 12 R-R intervals continues to be updated, the opportunities for changing from the concerned state 304 to another state and the estimates of heart rate only occur once the three-second timer expires. Upon initial entry to the concerned state 304, it is advantageous to process the most recent three-seconds of ECG data, i.e., ECG data for the three seconds leading up to the transition to the concerned state 304. This requires a continuous circular buffering of the most recent three seconds of ECG data even while in the not concerned state 302.

While in the concerned state 304, the present invention determines how sinusoidal and how noisy the signals are in order to determine the likelihood that a ventricular fibrillation (VF) or fast ventricular tachycardia (VT) event is taking place, since the more sinusoidal and low noise the signal is, the more likely a VT/VF event is taking place. As illustrated in FIG. 4, once the device transitions from the not concerned state 302 to the concerned state 304, Block 305, a buffer for each of the two channels ECG 1 and ECG2 for storing classifications of 3-second segments of data as "shockable" or "non-shockable" is cleared. Processing of signals of the two channels ECG1 and ECG2 while in the concerned state 304 is then triggered by the three second time period, rather than by the sensing of an R-wave utilized during the not concerned state 302.

Once the three second time interval has expired, YES in Block 341, morphology characteristics of the signal during the three second time interval for each channel are utilized to determine whether the signals are likely corrupted by noise artifacts and to characterize the morphology of the signal as "shockable" or "not shockable". For example, using the signals associated with the three second time interval, a determination is made for each channel ECG1 and ECG 2 as to whether the channel is likely corrupted by noise, Block 342, and a determination is then made as to whether both channels ECG1 and ECG2 are corrupted by noise, Block 344.

Figure 5:
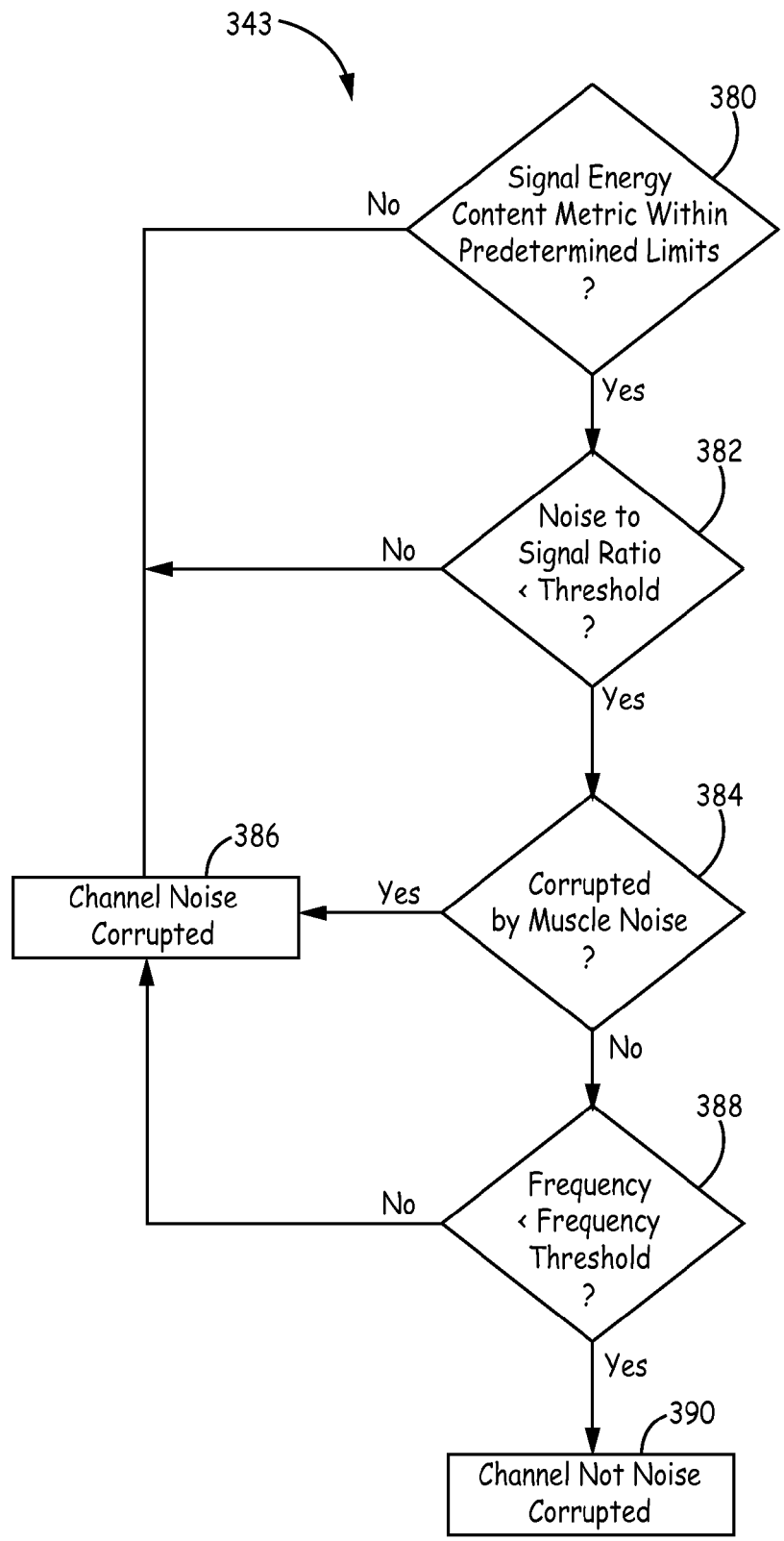
FIG. 5 is a flowchart of a method of determining noise according to an embodiment of the present disclosure.

FIG. 5 is a flowchart of a method of determining noise according to an embodiment of the present disclosure. As illustrated in FIG. 5, the determination as to whether the signal associated with each of the channels ECG1 and ECG2 is likely corrupted by noise, Block 342 of FIG. 4, includes multiple sequential noise tests that are performed on each channel ECG and ECG2. During a first noise test, for example, a determination is made as to whether a metric of signal energy content of the signal for the channel is within predetermined limits, Block 380. For example, the amplitude of each sample associated with the three second window is determined, resulting in N sample amplitudes, from which a mean rectified amplitude is calculated as the ratio of the sum of the rectified sample amplitudes to the total number of sample amplitudes N for the segment. If the sampling rate is 256 samples per second, for example, the total number of sample amplitudes N for the three-second segment would be N=768 samples.

Once the mean rectified amplitude is calculated, a determination is made as to whether the mean rectified amplitude is between an upper average amplitude limit and a lower average amplitude limit, the lower average amplitude limit being associated with asystole episodes without artifact and the upper average amplitude limit being associated with a value greater than what would be associated with ventricular tachycardia and ventricular fibrillation events. According to an embodiment of the present invention, the upper average amplitude limit is set as 1.5 mV, and the lower average amplitude limit is set as 0.013 mV. While the metric of signal energy content is described above as the mean rectified amplitude, it is understood that other signal of energy contents could be utilized.

If the determined mean rectified amplitude is not between the upper average amplitude limit and the lower average amplitude limit, the three second segment for that channel is identified as being likely corrupted with noise, Block 386, and no further noise tests are initiated for that channel's segment.

If the determined mean rectified amplitude is located between the upper average amplitude limit and the lower average amplitude limit, a noise to signal ratio is calculated and a determination is made as to whether the noise to signal ratio is less than a predetermined noise to signal threshold, Block 382. For example, the amplitude of each sample associated with the three second window is determined, resulting in N raw sample amplitudes. The raw signal is lowpass filtered, resulting in L lowpass sample amplitudes. The raw mean rectified amplitude is determined as the average of the absolute values of the raw sample amplitudes. The lowpass mean rectified amplitude is determined as the average of the absolute values of the lowpass sample amplitudes. Next, a highpass mean rectified amplitude is then calculated as the difference between the raw mean rectified amplitude and the lowpass mean rectified amplitude. The noise to signal ratio is then determined as the ratio of the highpass mean rectified amplitude to the lowpass mean rectified amplitude. If the noise to signal ratio is greater than a predetermined threshold, such as 0.0703, for example, the three second segment for that channel is identified as being likely corrupted with noise, Block 386, and no further noise tests are initiated for the segment.

If the noise to signal ratio is less than or equal to the predetermined threshold, a determination is made as to whether the signal is corrupted by muscle noise, Block 384. According to an embodiment of the present invention, the determination as to whether the signal is corrupted by muscle noise is made by determining whether the signal includes a predetermined number of signal inflections indicative of the likelihood of the signal being corrupted by muscle noise, using a muscle noise pulse count that is calculated to quantify the number of signal inflections in the three second interval for each channel ECG1 and ECG2. The presence of a significant number of inflections is likely indicative of muscle noise.

Figure 6A:
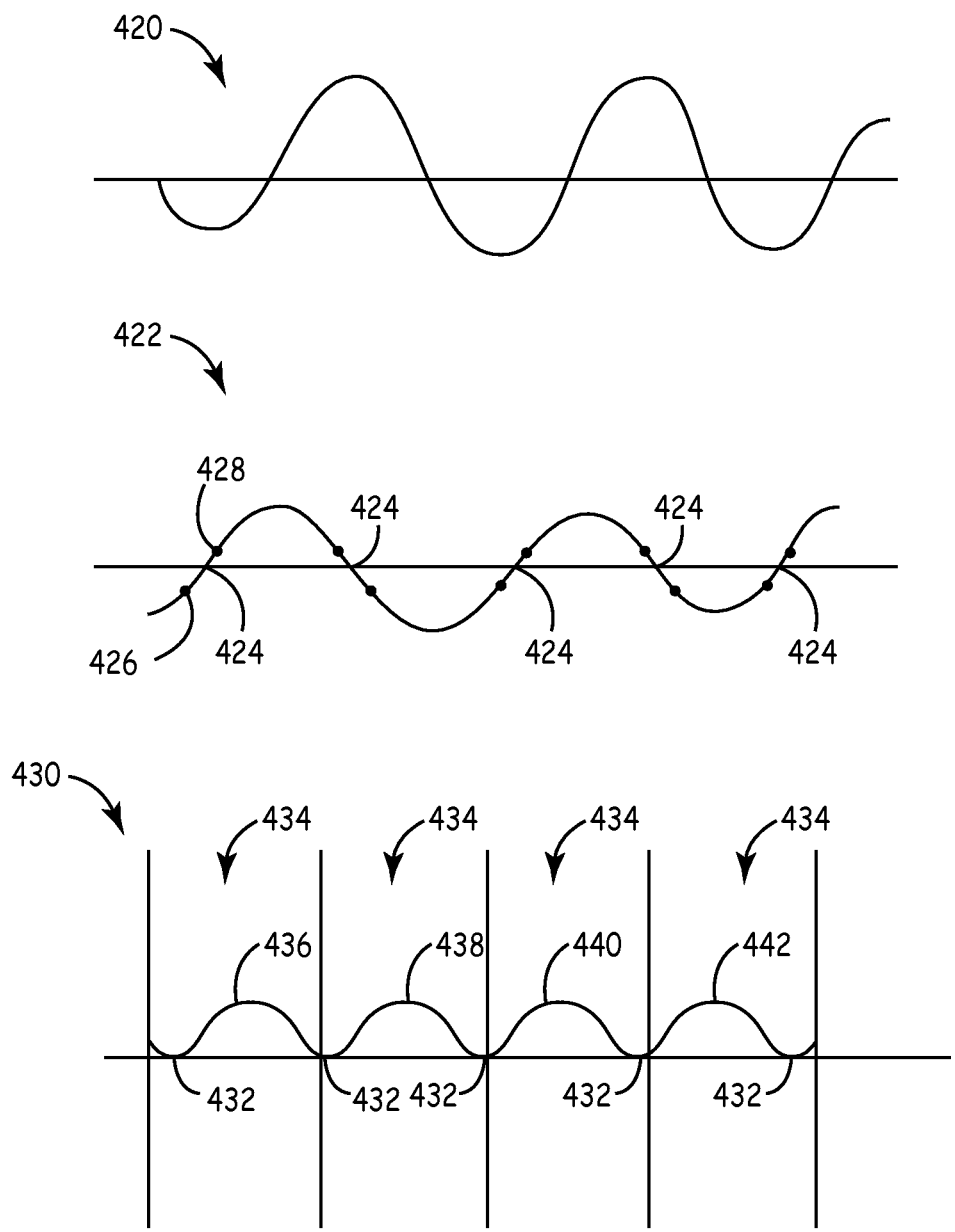
FIG. 6A is a graphical representation of a determination of whether a signal is corrupted by muscle noise according to an embodiment of the present invention.
Figure 6B:
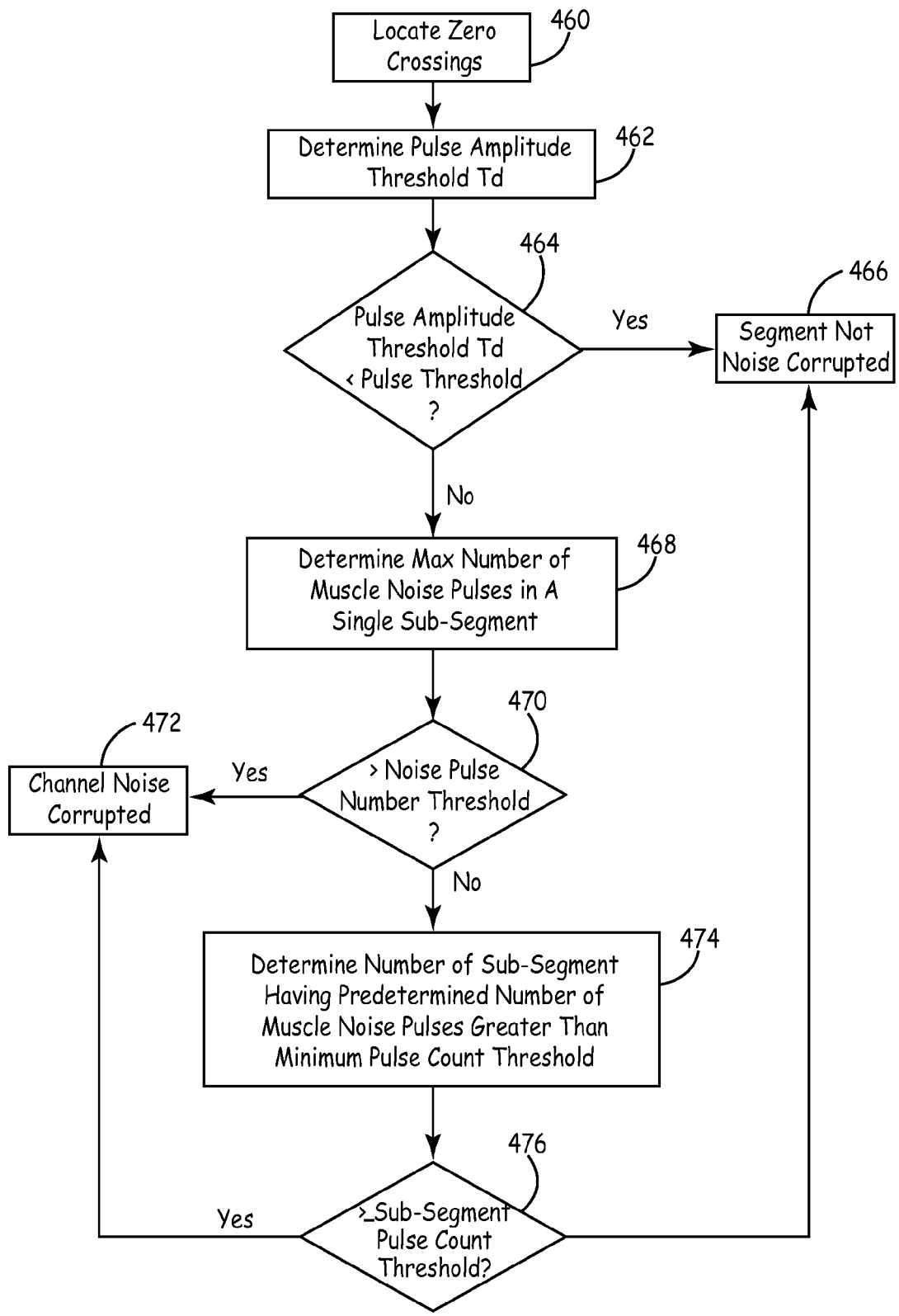
FIG. 6B is a flowchart of a method of determining whether a signal is corrupted by muscle noise according to an embodiment of the present invention.

FIG. 6A is a graphical representation of a determination of whether a signal is corrupted by muscle noise according to an embodiment of the present invention. FIG. 6B is a flowchart of a method of determining whether a signal is corrupted by muscle noise according to an embodiment of the present invention. For example, as illustrated in FIGS. 6A and 6B, in order to determine a muscle noise count for the three second interval, the raw signal 420 is applied to a first order derivative filter to obtain a derivative signal 422, and all of the zero-crossings 424 in the derivative signal 422 are located, Block 460. A data pair corresponding to the data points immediately prior to and subsequent to the zero crossings 424, points 426 and 428 respectively, for each crossing is obtained. The value of the data point in each data pair with smaller absolute value is zeroed in order to allow a clear demarcation of each pulse when a rectified signal 430 is derived from the derivative signal 422 with zeroed zero-crossing points 432.

A pulse amplitude threshold Td, for determining whether the identified inflection is of a significant amplitude to be identified as being associated with muscle noise, is determined, Block 462, by dividing the rectified signal from the three second segment into equal sub-segments 434, estimating a local maximum amplitude 436-442 for each of the sub-segments 434, and determining whether the local amplitudes 436-442 are less than a portion of the maximum amplitude, which is maximum amplitude 440 in the example of FIG. 6A, for the whole three second segment. If the local maximum amplitude is less than the portion of the maximum amplitude for the whole three second segment, the local maximum amplitude is replaced by the maximum for the whole three second segment for the sub-segment corresponding to that local maximum amplitude.

It is understood that while only two or less zero-crossing points are shown as being located within the sub-segments in the illustration of FIG. 6A for the sake of simplicity, in fact each of the sub-segments 434, which have a length of approximately 750 milliseconds, will contain many inflections, such as every 25 milliseconds, for example.

According to an embodiment of the present invention, the three second segment is divided into four sub-segments and the local maximum amplitudes are replaced by the maximum amplitude for the whole segment if the local maximum amplitude is less than one fifth of the maximum amplitude for the whole segment. Once the determination of whether to replace the local maximum amplitudes for each of the sub-segments with the maximum amplitude for the whole segment is completed, the pulse amplitude threshold Td for the segment is set equal to a predetermined fraction of the mean of the local maximum amplitudes for each of the sub-segments. According to an embodiment of the present invention, the pulse amplitude threshold Td for the three second segment is set equal to one sixth of the mean of the local maximum amplitudes 436-440.

Once the pulse amplitude threshold Td has been determined, the inflections associated with the signal for the three second segment is classified as being of significant level to be likely indicative of noise by determining whether the pulse amplitude threshold Td is less than a pulse threshold, Block 464. According to an embodiment of the present invention, the pulse threshold is set as 1 microvolt. If the pulse amplitude threshold Td is less than the pulse threshold, the signal strength is too small for a determination of muscle noise, and therefore the signal is determined to be not likely corrupted by noise and therefore the channel is determined to be not noise corrupted, Block 466.

If the pulse amplitude threshold Td is greater than or equal to the pulse threshold, the three second segment is divided into twelve sub-segments of 250 ms window length, the number of muscle noise pulses in each sub-segment is counted, and both the sub-segment having the maximum number of muscle noise pulses and the number of sub-segments having 6 or more muscle noise pulses that are greater than a predetermined minimum threshold is determined. Muscle noise is determined to be present in the signal if either the maximum number of muscle noise pulses in a single sub-segment is greater than a noise pulse number threshold or the number of sub-segments of the twelve sub-segments having 6 or more muscle noise pulses greater than the minimum threshold is greater than or equal to a sub-segment pulse count threshold. According to an embodiment of the present invention, the noise pulse number threshold is set equal to eight and the sub-segment pulse count threshold is set equal to three.

For example, if the pulse amplitude threshold Td is greater than or equal to the pulse threshold, No in Block 464, the maximum number of muscle noise counts in a single sub-segment is determined, Block 468. If the maximum number of muscle noise counts is greater than the noise pulse number threshold, Yes in Block 470, the channel is determined to be noise corrupted, Block 472. If the maximum number of muscle noise counts for the channel is less than or equal to the noise pulse number threshold, No in Block 470, the number of sub-segments of the twelve sub-segments having 6 or more muscle noise pulses greater than the minimum threshold is determined, Block 474, and if the number is greater than or equal to a sub-segment pulse count threshold, Yes in Block 476, the channel is determined to be noise corrupted, Block 472. If the number is less than the sub-segment pulse count threshold, No in Block 476, the channel is determined not to be noise corrupted, Block 466.

Figure 6C:
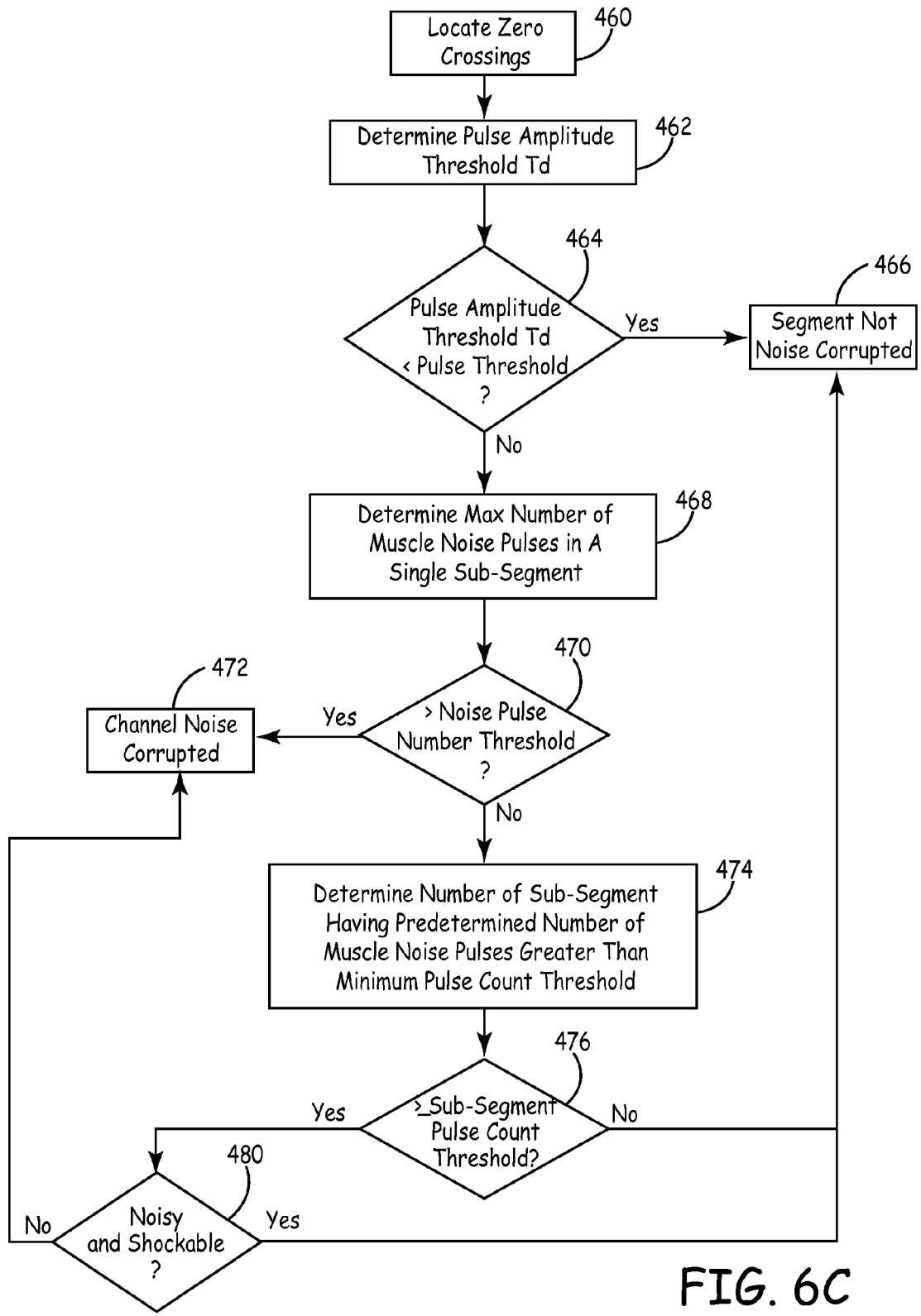
FIG. 6C is a flowchart of a method of determining whether a signal is corrupted by muscle noise according to an embodiment of the present invention.

FIG. 6C is a flowchart of a method of determining whether a signal is corrupted by muscle noise according to an embodiment of the present invention. Since muscle noise can be present during an episode of ventricular tachycardia, the width of the overall signal pulse waveform is determined in order to distinguish between signals that are determined likely to be purely noise related and signals that are both shockable events and determined to include noise. Therefore, as illustrated in FIG. 6C, according to an embodiment of the present invention, once muscle noise is determined to be present as a result of the muscle noise pulse count being satisfied, No in Block 470 and Yes in Block 476, a determination is made as to whether the signal is both noise corrupted and shockable, Block 480.

According to an embodiment of the present invention, the determination in Block 480 as to whether the signal is both noisy and shockable is made, for example, by dividing the rectified signal, having 768 data points, into four sub-segments and determining a maximum amplitude for each of the four sub-segments by determining whether a maximum amplitude for the sub-segment is less than a portion of the maximum amplitude for the entire rectified signal in the three second segment. For example, a determination is made for each sub-segment as to whether the maximum amplitude for the sub-segment is less than one fourth of the maximum amplitude for the entire rectified signal. If less than a portion of the maximum amplitude for the entire rectified signal in the three second segment, the maximum amplitude for the sub-segment is set equal to the maximum amplitude for the entire rectified signal.

A mean rectified amplitude for each of the sub-segments is determined by dividing the sum of the rectified amplitudes for the sub-segment by the number of samples in the sub-segment, i.e., 768÷4. Then the normalized mean rectified amplitude for each sub-segment is determined by dividing the mean rectified amplitude for each of the sub-segments by the peak amplitude for the sub-segment. The normalized mean rectified amplitude for the three second segment is then determined as the sum of the normalized mean rectified amplitudes for each sub-segment divided by the number of sub-segments, i.e., four.

Therefore, once muscle noise is suspected as a result of the determination of the muscle noise pulse count, the determination of Block 480 based on whether the normalized mean rectified amplitude for the three second segment is greater than a predetermined threshold for identifying signals that, despite being indicative of a likelihood of being associated with noise, nevertheless are associated with a shockable event. For example, according to an embodiment of the present invention, a determination is made as to whether the normalized mean rectified amplitude for the three second segment is greater than 18 microvolts. If the normalized mean rectified amplitude for the three second segment is less than or equal to the predetermined threshold, the channel is likely corrupted by muscle noise and not shockable, No in Block 480, and is therefore identified as being corrupted by noise, Block 472. If the normalized mean rectified amplitude for the three second segment is greater than the predetermined threshold, the channel is determined to be likely corrupted by muscle noise and shockable, Yes in Block 480, and is therefore identified as not to be likely corrupted by muscle noise, Block 478.

Returning to FIG. 5, when the signal is determined to be not likely corrupted by muscle noise, a determination is made as to whether the mean frequency of the signal associated with the channel is less than a predetermined mean frequency threshold, Block 388, such as 11 Hz for example. The mean frequency of the signal during the 3 second segment for each channel ECG 1 and ECG2 is generated, for example, by calculating the ratio of the mean absolute amplitude of the first derivative of the 3 second segment to the mean absolute amplitude of the 3 second segment, multiplied by a constant scaling factor. If the mean frequency is determined to be greater than or equal to the predetermined mean frequency threshold, No in Block 388, the three second segment for that channel is identified as being likely corrupted with noise, Block 386. If the mean frequency is determined to be less than the predetermined mean frequency threshold, Yes in Block 388, the three second segment for that channel is identified as being not noise corrupted, Block 390.

According to an embodiment of the present invention, since the mean spectral frequency tends to be low for true ventricular fibrillation events, moderate for organized rhythms such as sinus rhythm and supraventricular tachycardia, for example, and high during asystole and noise, the determination in Block 388 includes determining whether the mean frequency is less than a predetermined upper mean frequency threshold, such as 11 Hz (i.e., mean period T of approximately 91 milliseconds) for example, and whether the mean frequency is less than a predetermined lower mean frequency, such as 3 Hz for example. If the mean frequency is below a second, lower threshold, such as 3 Hz, for example, the signal is also rejected as noise and no further noise tests are initiated. This comparison of the mean frequency to a second lower threshold is intended to identify instances of oversensing, resulting in appropriate transition to the concerned state. If the mean frequency of the signal is less than 3 Hz, it is generally not possible for the heart rate to be greater than 180 beats per minute. In practice, it may be advantageous to set the lower frequency threshold equal to the programmed VT/VF detection rate, which is typically approximately 3 Hz.

Therefore, in the determination of Block 388, if the mean frequency is determined to be either greater than or equal to the predetermined upper mean frequency threshold or less than the lower threshold, the three second segment for that channel is identified as being likely corrupted with noise, Block 386. If the mean frequency is determined to be both less than the predetermined upper mean frequency threshold and greater than the lower threshold, the three second segment for that channel is identified as not being noise corrupted, Block 390.

Returning to FIG. 4, once the determination as to whether the channels ECG1 and ECG2 are corrupted by noise is made, Block 342, a determination is made as to whether both channels are determined to be noise corrupted, Block 344. If the signal associated with both channels ECG1 and ECG2 is determined to likely be corrupted by noise, both channels are classified as being not shockable, Block 347, and therefore a buffer for each channel ECG1 and ECG 2 containing the last three classifications of the channel is updated accordingly and the process is repeated for the next three-second windows. If both channels ECG1 and ECG2 are not determined to be likely corrupted by noise, No in Block 344, the device distinguishes between either one of the channels being not corrupted by noise or both channels being not corrupted by noise by determining whether noise was determined to be likely in only one of the two channels ECG1 and ECG2, Block 346.

If noise was likely in only one of the two channels, a determination is made whether the signal for the channel not corrupted by noise, i.e., the clean channel, is more likely associated with a VT event or with a VF event by determining, for example, whether the signal for that channel includes R-R intervals that are regular and the channel can be therefore classified as being relatively stable, Block 348. If the R-R intervals are determined not to be relatively stable, NO in Block 348, the signal for that channel is identified as likely being associated with VF, which is then verified by determining whether the signal is in a VF shock zone, Block 350, described below. If R-R intervals for that channel are determined to be stable, YES in Block 348, the signal is identified as likely being associated with VT, which is then verified by determining whether the signal is in a VT shock zone, Block 352, described below.

If noise was not likely for both of the channels, No in Block 346, i.e., both channels are determined to be clean channels, a determination is made whether the signal for both channels is more likely associated with a VT event or with a VF event by determining whether the signal for both channels includes R-R intervals that are regular and can be therefore classified as being relatively stable, Block 356. The determination in Block 356 of whether the R-R intervals are determined to be relatively stable may be made using the method described in U.S. Pat. No. 7,894,894 to Stadler et al., incorporated herein by reference in it's entirety. If the R-R intervals are determined not to be relatively stable, NO in Block 356, the signal for both channels is identified as likely being associated with VF, which is then verified by determining whether the signal for each channel is in a VF shock zone, Block 360, described below. If R-R intervals for both channels are determined to be stable, YES in Block 356, the signal is identified as likely being associated with VT, which is then verified by determining, based on both channels, whether the signal is in a VT shock zone, Block 358.

Figure 7:
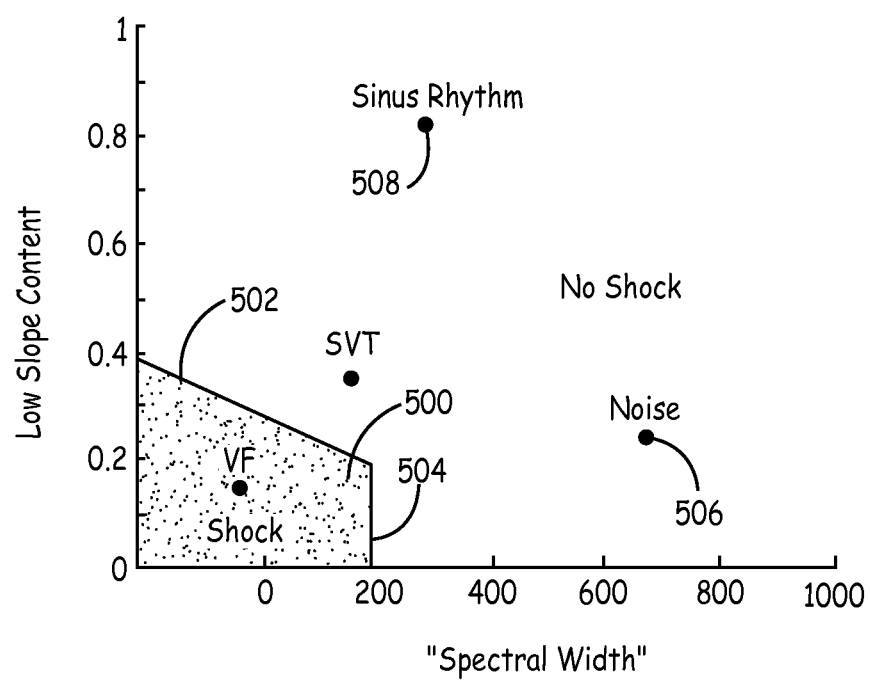
FIG. 7 is a graphical representation of a VF shock zone according to an embodiment of the present invention.

FIG. 7 is a graphical representation of a VF shock zone according to an embodiment of the present invention. As illustrated in FIG. 7, a VF shock zone 500 is defined for each channel ECG1 and ECG2 based on the relationship between the calculated low slope content and the spectral width associated with the channel. For example, the shock zone is defined by a first boundary 502 associated with the low slope content set for by the equation:

$$\text{Low slope content} = -0.0013 \times \text{spectral width} + 0.415 \quad \text{Equation 1}$$

and a second boundary 504 associated with the spectral width set forth by the equation:

$$\text{spectral width} = 200 \quad \text{Equation 2}$$

The low slope content metric is calculated as the ratio of the number of data points with low slope to the total number of samples in the 3-second segment. For example, according to an embodiment of the present invention, the difference between successive ECG samples is determined as an approximation of the first derivative (i.e, the slope) of the ECG signal. In particular, the raw signal for each channel is applied to a first order derivative filter to obtain a derivative signal for the three-second segment. The derivative signal is then rectified, divided into four equal sub-segments, and the largest absolute slope is estimated for each of the four sub-segments.

A determination is made as to whether the largest absolute slopes are less than a portion of the overall largest absolute slope for the whole three-second segment, such as one-fifth of the overall absolute slope, for example. If the largest absolute slope is less than the portion of the overall slope, then the slope value for that sub-segment is set equal to the overall largest absolute slope. If the largest absolute slope is not less than the portion of the overall slope, then the slope value for that sub-segment is set equal to the determined largest absolute slope for the sub-segment.

Once the slope value for each of the sub-segments has been determined and updated by being set equal to the largest slope for the three second segment, if necessary, the average of the four slopes is calculated and divided by a predetermined factor, such as 16 for example, to obtain a low slope threshold. The low slope content is then obtained by determining the number of sample points in the three-second segment having an absolute slope less than or equal to the low slope threshold.

According to an embodiment of the present invention, if, during the determination of the low slope threshold, the low slope threshold is a fraction, rather than a whole number, a correction is made to the low slope content to add a corresponding fraction of the samples. For example, if the threshold is determined to be 4.5, then the low slope content is the number of sample points having an absolute slope less than or equal to 4 plus one half of the number of sample points with slope equal to 5.

The spectral width metric, which corresponds to an estimate of the spectral width of the signal for the three-second segment associated with each channel ECG1 and ECG2, is defined, for example, as the difference between the mean frequency and the fundamental frequency of the signal. According to an embodiment of the present invention, the spectral width metric is calculated by determining the difference between the most recent estimate of the RR-cycle length and the mean spectral period of the signal for that channel. As is known in the art, the mean spectral period is the inverse of the mean spectral frequency.

As can be seen in FIG. 7, since noise 506 tends to have a relatively higher spectral width, and normal sinus rhythm 508 tends to have a relatively higher low slope content relative to VF, both noise 506 and normal sinus rhythm 508 would be located outside the VF shock zone 500.

A determination is made for each channel ECG1 and ECG2 as to whether the low slope content for that channel is less than both the first boundary 502 and the spectral width is less than the second boundary 504, i.e., the low slope content is less than −0.0013×spectral width+0.415, and the spectral width is less than 200. For example, once the event is determined to be associated with VF, i.e., the intervals for both channels are determined to be irregular, No in Block 356, a determination is made that channel ECG1 is in the VF shock zone, Yes in Block 360, if, for channel ECG1, both the low slope content is less than the first boundary 502 and the spectral width is less than the second boundary 504. The three second segment for that channel ECG1 is then determined to be shockable, Block 363 and the associated buffer for that channel is updated accordingly. If either the low slope content for the channel is not less than the first boundary 502 or the spectral width is not less than the second boundary, the channel ECG1 is determined not to be in the VF shock zone, No in Block 360, the three second segment for that channel ECG1 is then determined to be not shockable, Block 365, and the associated buffer is updated accordingly.

Similarly, a determination is made that channel ECG2 is in the VF shock zone, Yes in Block 362, if, for channel ECG2, both the low slope content is less than the first boundary 502 and the spectral width is less than the second boundary 504. The three second segment for that channel ECG2 is then determined to be shockable, Block 369 and the associated buffer for that channel is updated accordingly. If either the low slope content for the channel is not less than the first boundary 502 or the spectral width is not less than the second boundary, the channel ECG2 is determined not to be in the VF shock zone, No in Block 362, the three second segment for that channel ECG2 is then determined to be not shockable, Block 367, and the associated buffer is updated accordingly.

Figure 8A:
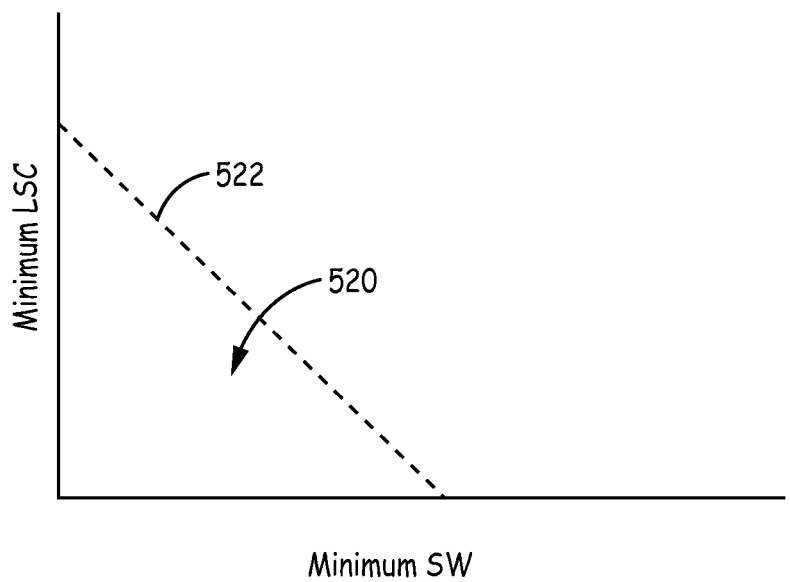
FIGS. 8A and 8B are graphical representations of the determination of whether an event is within a shock zone according to an embodiment of the present invention.
Figure 8B:
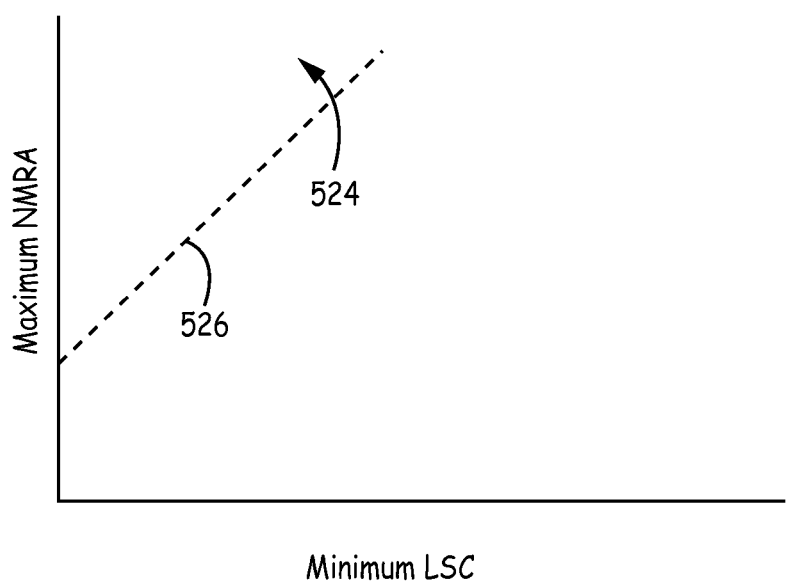

FIGS. 8A and 8B are graphical representations of the determination of whether an event is within a shock zone according to an embodiment of the present invention. During the determination of whether the event is within the VT shock zone, Block 358 of FIG. 4, the low slope content and the spectral width is determined for each channel ECG1 and ECG2, as described above in reference to determining the VF shock zone. A determination is made as to which channel of the two signal channels ECG1 and ECG2 contains the minimum low slope content and which channel of the two signal channels ECG1 and ECG2 contains the minimum spectral width. A first VT shock zone 520 is defined based on the relationship between the low slope content associated with the channel determined to have the minimum low slope content and the spectral width associated with the channel determined to have the minimum spectral width. For example, according to an embodiment of the present invention, the first VT shock zone 520 is defined by a boundary 522 associated with the minimum low slope content and the minimum spectral width set forth by the equation:

$$LSC = -0.004 \times SW + 0.93 \qquad \text{Equation 3}$$

A second VT shock zone 524 is defined based on the relationship between the low slope content associated with the channel determined to have the minimum low slope content and the normalized mean rectified amplitude associated with the channel determined to have the maximum normalized mean rectified amplitude. In order to determine the normalized mean rectified amplitudes for the two channels ECG1 and ECG2 utilized during the VT shock zone test, the amplitude of each sample associated with the three second window is determined, resulting in N sample amplitudes, from which a mean rectified amplitude is calculated as the ratio of the sum of the rectified sample amplitudes to the total number of sample amplitudes N for the segment. If the sampling rate is 256 samples per second, for example, the total number of sample amplitudes N for the three-second segment would be N=768 samples.

According to an embodiment of the present invention, for example, the second VT shock zone 524 is defined by a second boundary 526 associated with the relationship between the minimum low slope count and the maximum normalized mean rectified amplitude set forth by the equation:

$$NMRA = 68 \times LSC + 8.16 \qquad \text{Equation 4}$$

If both the minimum low slope count is less than the first boundary 522, i.e., −0.004×minimum spectral width+0.93, and the maximum normalized mean rectified amplitude is greater than the second boundary 526, i.e., 68×minimum low slope count+8.16, the event is determined to be in the VT shock zone, YES in Block 358, and both channels ECG1 and ECG2 are determined to be shockable, Block 357, and the associated buffers are updated accordingly. If either the minimum low slope count is not less than the first boundary 522 or the maximum normalized mean rectified amplitude is not greater than the second boundary 526, the event is determined to be outside the VT shock zone, NO in Block 358, and both channels ECG1 and ECG2 are determined to be not shockable, Block 359.

As described, during both the VF shock zone test, Blocks 360 and 362, and the VT shock zone test, Block 358, the test results for each channel ECG1 and ECG2 as being classified as shockable or not shockable are stored in a rolling buffer containing the most recent eight such designations, for example, for each of the two channels ECG1 and ECG2 that is utilized in the determination of Block 356, as described below.

If only one of the two channels ECG1 and ECG2 is determined to be corrupted by noise, Yes in Block 346, a determination is made whether the signal for the channel not corrupted by noise, i.e., the "clean channel", is more likely associated with a VT event or with a VF event by determining whether the signal for the clean channel includes R-R intervals that are regular and can be therefore classified as being relatively stable, Block 348. If the R-R intervals are determined not to be relatively stable, NO in Block 348, the signal for the clean channel is identified as likely being associated with VF, which is then verified by determining whether the signal for the clean channel is in a VF shock zone, Block 350, described below. If R-R intervals for the clean channel are determined to be stable, YES in Block 348, the signal is identified as likely being associated with VT, which is then verified by determining whether the signal for the clean channel is in a VT shock zone, Block 352.

Figure 9:
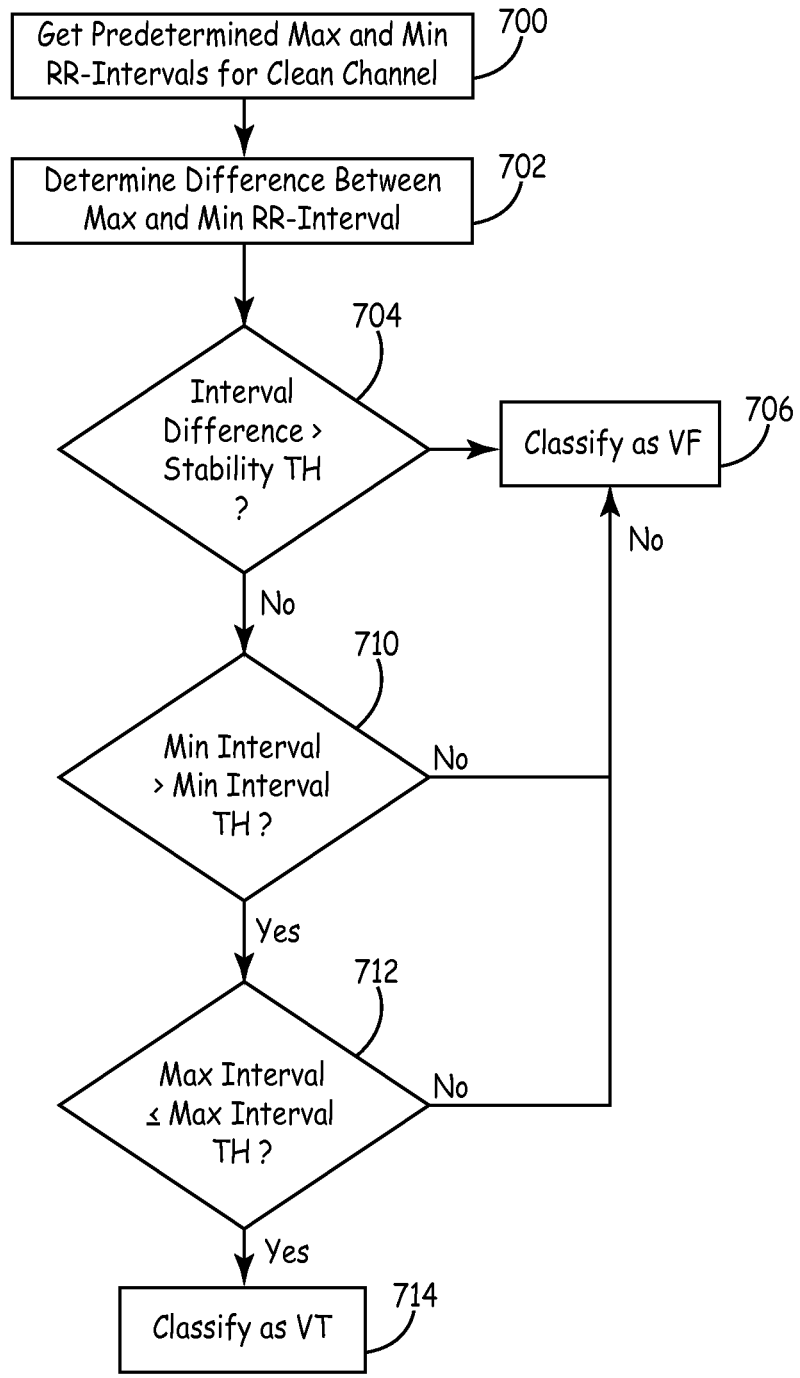
FIG. 9 is a flowchart of a method for discriminating cardiac events according to an embodiment of the disclosure.

According to an embodiment of the present invention, in order to determine whether the signal for the clean channel includes R-R intervals that are regular and the clean channel can be therefore classified as being either relatively stable, Yes in Block 348, or relatively unstable, No in Block 348, the device discriminates VT events from VF events in Block 348 by determining whether the relative level of variation in the RR-intervals associated with the clean channel is regular. FIG. 9 is a flowchart of a method for discriminating cardiac events according to an embodiment of the disclosure. For example, as illustrated in FIG. 9, predetermined maximum and minimum intervals for the clean channel are identified from the updated buffer of 12 RR-intervals, Block 342 of FIG. 4. According to an embodiment of the present invention, the largest RR-interval and the sixth largest RR-interval of the twelve RR-intervals are utilized as the maximum interval and the minimum interval, respectively.

The difference between the maximum RR-interval and the minimum RR-interval of the 12 RR-intervals is calculated to generate an interval difference associated with the clean channel, 702. A determination is then made as to whether the interval difference is greater than a predetermined stability threshold, Block 704, such as 110 milliseconds, for example.

If the interval difference is greater than the stability threshold, the event is classified as an unstable event, Block 706, and therefore the clean channel is determined not to include regular intervals, No in Block 348, and a determination is made as to whether the signal associated with the clean channel is within a predetermined VF shock zone, Block 350 of FIG. 4, described below. If the interval difference is less than or equal to the stability threshold, No in Block 704, the device determines whether the minimum RR interval is greater than a minimum interval threshold, Block 710, such as 200 milliseconds, for example.

If the minimum interval is less than or equal to the minimum interval threshold, No in Block 710, the event is classified as an unstable event, Block 706, and therefore the clean channel is determined not to include regular intervals, No in Block 348, and a determination is made as to whether the signal associated with the clean channel is within a predetermined VF shock zone, Block 350 of FIG. 4, described below. If the minimum interval is greater than the minimum interval threshold, Yes in Block 710, the device determines whether the maximum interval is less than or equal to a maximum interval threshold, Block 712, such as 333 milliseconds for example. If the maximum interval is greater than the maximum interval threshold, the event is classified as an unstable event, Block 706, and therefore the clean channel is determined not to include regular intervals, No in Block 348, and a determination is made as to whether the signal associated with the clean channel is within a predetermined VF shock zone, Block 350 of FIG. 4, described below. If the maximum interval is less than or equal to the maximum interval threshold, the event is classified as a stable event, Block 714, and therefore the clean channel is determined to include regular intervals, Yes in Block 348, and a determination is made as to whether the signal associated with the clean channel is within a predetermined VT shock zone, Block 352 of FIG. 4, described below.

Returning to FIG. 4, the determination of whether the clean channel is within the VF shock zone, Block 350, is made based upon a low slope content metric and a spectral width metric, similar to the VF shock zone determination described above in reference to Blocks 360 and 362, both of which are determined for the clean channel using the method described above. Once the low slope content metric and a spectral width metric are determined for the clean channel, the determination of whether the clean channel is in the VF shock zone is made using Equations 1 and 2, so that if either the low slope content for the clean channel is not less than the first boundary 502 or the spectral width is not less than the second boundary 504, the clean channel is determined not to be in the VF zone, No in Block 350 and both channels are classified as not shockable, Block 351, and the associated buffers are updated accordingly.

If the low slope content for the clean channel is less than the first boundary 502 and the spectral width is less than the second boundary 504, the clean channel is determined to be in the VF zone, Yes in Block 350. A determination is then made as to whether the channel determined to be corrupted by noise, i.e., the "noisy channel", is within the VF shock zone, Block 354. If either the low slope content for the noisy channel is not less than the first boundary 502 or the spectral width is not less than the second boundary 504, the noisy channel is determined not to be in the VF zone, No in Block 354, the clean channel is classified as shockable and the noisy channel is classified as not shockable, Block 355, and the associated buffers are updated accordingly.

If the low slope content for the noisy channel is less than the first boundary 502 and the spectral width is less than the second boundary 504, the noisy channel is determined to be in the VF zone, Yes in Block 354, both the clean channel and the noisy channel are classified as being shockable, Block 353, and the associated buffers are updated accordingly.

Similar to the VT shock zone determination described above in reference to Block 358, during the determination as to whether the clean channel is within the VT shock zone in Block 352, the low slope content and the spectral width is determined for the clean channel as described above in reference to determining the VF shock zone. The first VT shock zone 520 is defined based on the relationship between the low slope content and the spectral width associated with the clean channel according to Equation 3, for example, and the second VT shock zone 524 is defined based on the relationship between the low slope count and the normalized mean rectified amplitude associated with the clean channel. The normalized mean rectified amplitudes for the clean channel is the same as described above in reference to the noise detection tests of Block 344. For example, according to an embodiment of the present invention, the second VT shock zone 524 is defined by a second boundary 526 associated with the relationship between the low slope count and the normalized mean rectified amplitude of the clean channel using Equation 4.

If both the low slope count is less than the first boundary 522, i.e., $-0.004 \times$ spectral width of clean channel$+0.93$, and the normalized mean rectified amplitude is greater than the second boundary 526, i.e., $68 \times$ low slope count of clean channel$+8.16$, the clean channel is determined to be in the VT shock zone, Yes in Block 352, both channels are classified as being shockable, Block 353, and the associated buffers are updated accordingly.

If either the low slope count is not less than the first boundary 522 or the maximum normalized mean rectified amplitude is not greater than the second boundary 526, the clean channel is determined to be outside the VT shock zone, No in Block 352, both channels are classified as being not shockable, Block 351, and the associated buffers are updated accordingly.

According to an embodiment of the present disclosure, in addition to the classification of the sensing channels ECG1 and ECG2 as being shockable or not shockable using a gross morphology analysis, as described in FIG. 4, for example, the device also performs a beat-based analysis of the beats within each of the three-second windows, Block 368, so that the decision on state transitions (e.g. as to whether to transition from the concerned operating state 304 to the armed operating state 306 in Block 370, or from the armed state 306 to the shock state 308) is made based on the results of both an analysis of the gross morphology of the signal in the three-second window or windows for each sensing channel ECG1 and ECG2, and an analysis of the morphology of individual beats or R-waves in the three-second window or windows for each sensing channel ECG1 and ECG2, as described below.

For a three-second segment to be classified as shockable, both the gross morphology and beat-based analysis have to classify the same three-second segment as shockable.

According to an embodiment, the device also determines a confidence level measurement during the beat-based analysis, Block 368, to determine whether the beat-based analysis may be corrupted by noise, and therefore determine whether the beat-based classification is verified. In this way, the device performs two separate noise determinations of the same signal within the same sensing channels ECG1 and ECG2 for use in the state transition decision, one determination during the gross morphology analysis, Block 342-346, and the second determination during the beat-based analysis, Block 368.

For example, according to an embodiment of the present invention, in order to determine whether to transition from the concerned operating state 304 to the armed operating state 306, the device determines whether a predetermined number, such as two out of three for example, of three-second segments for both channels ECG1 and ECG2 have been classified as being shockable during the gross morphology analysis, Blocks 353, 357, 363 and 369, and determines whether those three-second segments for both channels have also been classified as being shockable during the beat-based analysis, and/or whether the beat-based analysis for one or both of the channels may be corrupted by noise, Block 368. If the predetermined number of three-second segments in both channels ECG1 and ECG2 have been classified as shockable during both the gross morphology analysis and the beat-based analysis and noise determination, the device transitions from the concerned state 304 to the armed state 306, Yes in Block 370. When the device determines to transition from the concerned state 304 to the armed state 306, Yes in Block 370, processing continues to be triggered by a three-second time out as is utilized during the concerned state 304, described above.

If the predetermined number of three-second segments in both channels ECG1 and ECG2 have not been classified as shockable during both the gross morphology analysis and the beat-based analysis, the device does not transition from the concerned state 304 to the armed state 306, No in Block 370, and a determination as to whether to transition back to the not concerned state 302 is made, Block 372. The determination as to whether to transition from the concerned state 304 back to the not concerned state 302 is made, for example, by determining whether a heart rate estimate is less than a heart rate threshold level in both of the two channels ECG1 and ECG2, using the method for determining a heart rate estimate as described in U.S. Pat. No. 7,894,894 to Stadler et al., incorporated herein by reference in it's entirety. If it is determined that the device should not transition to the not concerned state 302, i.e., either of the two heart rate estimates are greater than the heart rate threshold, No in Block 372, the process continues using the signal generated during a next three-second window, Block 341.

As described above, the determination of whether the sensing channels ECG1 and ECG2 are shockable or not shockable, Blocks 353, 355, 357, and 363-369, is performed by analyzing the gross morphology of a sensed waveform occurring within the three-second windows. The ECG signal is segmented into n-second intervals, i.e., 3 second intervals that are used for determining gross morphology features of the three-second waveform. In particular, the gross morphology features are determined across an n-second time interval without relying on R-wave sensing and are therefore features making up the whole waveform signal that can be determined from the ECG signal independent of individual cardiac signals of the cardiac cycle, i.e., individual beats or R-waves contained within the three-second window that are within the entire three-second window. A single waveform in the n-second window begins at the start of the window, extends through entire window, ending at the end of the three-second window so that a single morphology determination is made for the single waveform included within the single three-second window.

On the other hand, multiple cardiac cycles, i.e, R-waves signals, are included within the three-second window, and therefore the n-second window may start and end at any time point relative to each of the individual R-wave signals irrespective of where an individual R-wave signal starts and ends, so that multiple individual beat-based determinations are made during the beat-based analysis for the multiple beat waveforms included within the single three-second window.

Morphology features computed for the single waveform extending across the n-second time period are referred to as "gross" morphology features because the features are characteristics of the single signal, extending from the start to the end of the window, that is extracted, independent of cardiac cycle timing, from a time segment that includes multiple individual cardiac cycles. In contrast, morphology features extracted from the ECG signal during a cardiac cycle are referred to as "beat-based" features. Beat-based features are determined from an ECG signal segment over a time interval of one cardiac cycle of multiple cardiac cycles contained within a single three-second window. Beat-based features may be averaged or determined from multiple cardiac cycles but are representative of a single feature of the ECG signal during a cardiac cycle. Determination of a beat feature is dependent on identifying the timing of a cardiac cycle, or at least a sensed event such as an R-wave, as opposed to determining gross features independent of the cardiac cycle over a time segment that is typically longer than one cardiac cycle.

Therefore, as described above, in addition to performing the morphology analysis of the whole waveform within the three-second windows associated with each sensing channel ECG1 and ECG2, the device performs a beat-based analysis of the signal sensed simultaneously within both channels ECG1 and ECG2, and/or whether the beat-based analysis for one or both of the channels is likely corrupted by noise Block 368. During the beat-based analysis, individual beats located within a three-second window are compared to a stored template, such as a normal sinus rhythm template, for example, to determine whether individual beats should be classified as a match beat or a non-match beat. The template may be input within the device manually by a clinician through visual analysis of ECG signals, or may be generated by the device after being implanted in the patient. For example, according to one embodiment, the device may generate the template using a fourth order signal of a predetermined number of beats, as described in commonly assigned U.S. patent application Ser. No. 13/826,097, incorporated herein by reference in it's entirety.

Figure 10:
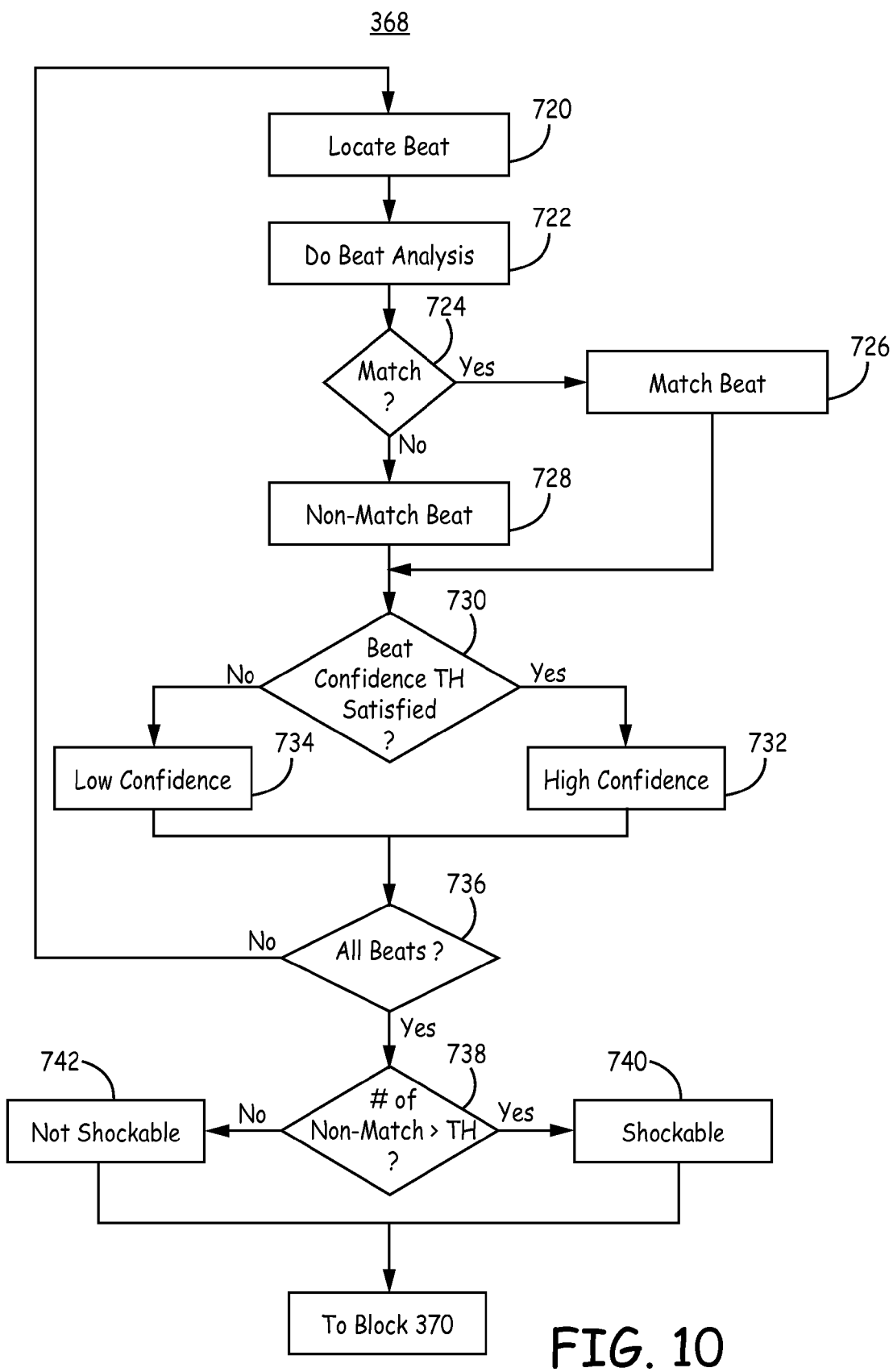
FIG. 10 is a flowchart of a method for performing beat-based analysis during detection of arrhythmias in a medical device, according to an embodiment of the present disclosure.

FIG. 10 is a flowchart of a method for performing beat-based analysis during detection of arrhythmias in a medical device, according to an embodiment of the present disclosure. Therefore, as described above, in addition to performing the morphology analysis of the whole waveform within the three-second windows associated with each sensing channel ECG1 and ECG2, the device performs a beat-based analysis of the signal sensed simultaneously within both channels ECG1 and ECG2, Block 368 of FIG. 4. In particular, as illustrated in FIG. 10, for each three-second sensing window associated with the respective sensing channels ECG1 and ECG2, the device locates a single beat, i.e., R-wave, of the multiple beats in the three-second window, Block 720, and performs a beat-based analysis of the single beat, Block 722. According to an embodiment, for example, during the beat-based analysis, Block 722, the device computes a normalized waveform area difference (NWAD) between the beat, also identified herein as "the unknown beat", and a predetermined beat template, such as a normal sinus rhythm template, for example, and determines whether the beat matches the template, Block 724, based on the determined normalized waveform area difference, as described below.

Using the results of the comparison of the beat to the template, the device determines whether the beat is either a match beat or a non-match beat, Block 724, by determining whether the beat matches the sinus rhythm template within a predetermined percentage, such as 60 percent, for example. If the beat matches the template by the predetermined percentage or greater, Yes in Block 726, the beat is identified as a match beat. If the beat matches the template by less than the predetermined percentage, No in Block 724, the beat is identified as a non-match beat, Block 728.

Figure 11:
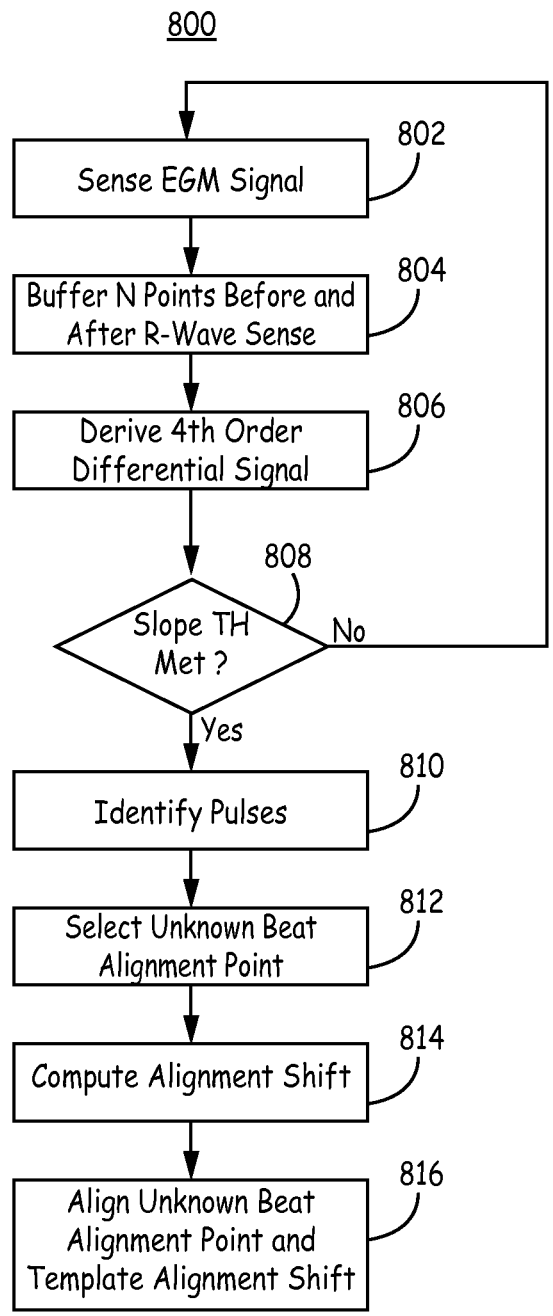
FIG. 11 is a flowchart of a method for aligning an ECG signal of an unknown beat with a known morphology template for beat-based analysis during detection of arrhythmias in a medical device, according to an embodiment of the present disclosure.

FIG. 11 is a flowchart of a method for aligning an ECG signal of an unknown beat with a known morphology template for beat-based analysis during detection of arrhythmias in a medical device, according to an embodiment of the present disclosure. In order to perform the comparison of the unknown beat with the template in Block 724 of FIG. 10 to identify the beat as being either a match beat or a non-match beat, the unknown beat must be aligned with the template. As illustrated in FIG. 11, during alignment of the unknown beat with the template, Block 800, the device identifies individual beats within the three-second window based on determined R-wave sense signals, Block 802, and for each beat stores n points before and n points after the sample point on which the R-wave sense occurs. The 2n+1 sample points define an alignment window within which an alignment point will be identified for alignment with the clinician input or device generated template, such as a normal sinus rhythm template, for example. In one embodiment, the alignment window is 53 sample points centered on the R-wave sense point. These sample points are stored in a memory buffer at block 804.

Once the sample points are determined for the beat, the device determines a fourth order difference signal for the beat from the buffered signal sample data, Block 806. The maximum slope of the fourth order difference signal is determined and compared to a maximum slope threshold, e.g. approximately 136 analog-to-digital (A/D) conversion units, Block 808. If the slope threshold is not met, No in Block 808, the signal may be rejected as a weak signal, no further analysis of that beat is performed, and the process continues with the next beat in the three-second window, Block 802. If the maximum slope is greater than the threshold, Yes in Block 808, indicating that at least one pulse corresponding to an R-wave is likely to be present in the alignment window, pulses associate with the individual beat within the alignment window are identified, Block 810.

To identify pulses associated with the beat within the alignment window, pulse criteria may be established, such as having a pulse width equal to at least some minimum number of sample points and a pulse amplitude of at least some minimum amplitude. The number of pulses identified, or lack thereof, within the alignment window may be used to reject a "cardiac cycle" as a noisy cycle or a weak signal. One or more pulses, including negative-going and positive-going pulses, may be identified according to amplitude and pulse width criteria. In some examples, a pulse may be identified based on a slope, maximum peak amplitude (positive or negative), pulse width or any combination thereof. If a threshold number of pulses is identified within the alignment window, the cycle may be considered a noisy cycle. While not shown explicitly in FIG. 11, a noisy cycle may be flagged or rejected for use in morphology analysis.

After identifying all pulses from the fourth order difference signal in the alignment window, a pulse having a maximum pulse amplitude and having the same polarity as a stored template alignment point is identified, Block 812. The sample point having the maximum pulse amplitude (absolute value) that also matches the polarity of the template alignment point is identified and defined as the unknown signal alignment point.

An alignment shift is computed, Block 814, as the difference in sample point number between the alignment point identified, Block 812, and the previously established template alignment point. The alignment shift is the number of sample points, that the unknown beat must be shifted in order to align the unknown signal alignment point with the template alignment point. The alignment shift is applied by shifting the unknown beat sample points to align the unknown beat and the template over the alignment window, Block 816. The alignment shift may be applied to the fourth order difference signal itself if the template is stored as an ensemble average of aligned fourth order difference signals or stored as the fourth order difference signal of an ensemble average of aligned raw ECG signals. The alignment shift may additionally or alternatively be applied to the digitized raw signal sample points of the unknown signal when the template is the ensemble average of the raw signal sample points acquired during a known rhythm and aligned using the fourth order difference signal, as described in the template generation described in commonly assigned U.S. patent application Ser. No. 13/826,097, incorporated herein by reference in it's entirety. In another variation, the template may be the fourth order difference signal of ensemble averaged raw signals, and the fourth order difference signal of the unknown raw signal is aligned with the fourth order difference template.

Figure 12:
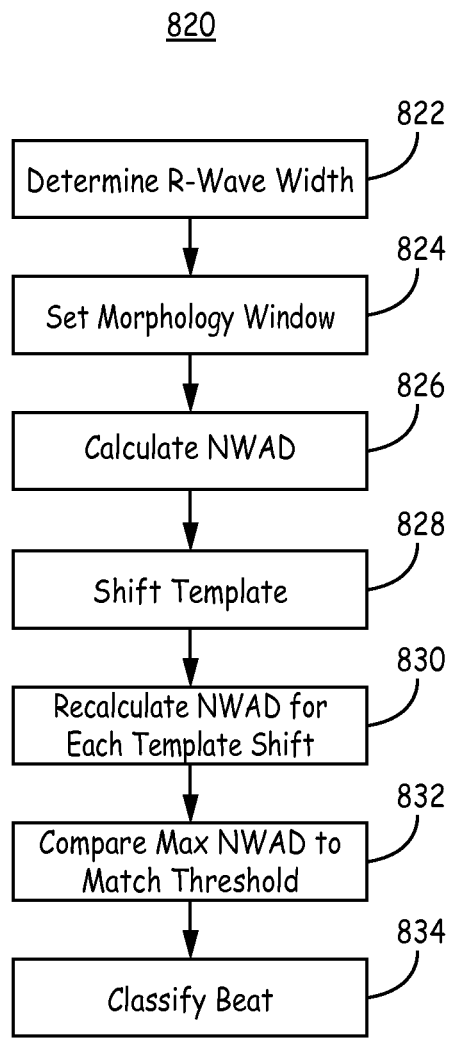
FIG. 12 is a flowchart of a method for computing a morphology metric to determine the similarity between a known template aligned with an unknown cardiac cycle signal according to one embodiment.

FIG. 12 is a flowchart of a method for computing a morphology metric to determine the similarity between a known template aligned with an unknown cardiac cycle signal according to one embodiment. After aligning the unknown beat and the template using the fourth order difference signal alignment points, the morphology between the unknown beat and the template is compared, Block 820. Numerous types of morphology analysis could be used, such as wavelet analysis, comparisons of fiducial points (peak amplitude, zero crossings, maximum slopes, etc.) or other techniques. In one embodiment, a NWAD is computed using a morphology analysis window that is a subset of, i.e. a number of sample points less than, the alignment window.

The operations performed by the device as described in conjunction with FIG. 12 may be performed on the aligned raw signal and corresponding template and/or the aligned fourth order difference signal and corresponding fourth order difference signal template.

As illustrated in FIG. 12, during the comparing of an individual beat with the beat template, the device determines the R-wave width of the unknown signal, Block 822. In an illustrative embodiment, in order to determine the R-wave width, the device determines an onset and an offset point of the R-wave. During the determination of the onset and offset, the maximum positive pulse and the maximum negative of the fourth order difference signal are identified. The maximum positive pulse is an identified pulse having positive polarity and maximum positive peak value; the maximum negative pulse is an identified pulse having negative polarity and maximum absolute peak value. If the R wave has a positive polarity in the raw ECG signal, the maximum positive pulse will precede the maximum negative pulse on the $4^{th}$-order difference waveform. An onset threshold is set based on the amplitude of the maximum positive pulse and an offset threshold is set based on the amplitude of the maximum negative pulse. For example, one-eighth of the peak amplitude of the maximum positive pulse may be defined as the onset threshold and one eighth of the negative peak amplitude of the maximum negative pulse may be defined as the offset threshold.

The onset of the R-wave is identified as the first sample point to the left of the maximum positive pulse (e.g. moving from the pulse peak backward in time to preceding sample points) to cross the onset threshold. The offset of the R-wave is identified as the first sample point to the right of the maximum negative pulse crossing the offset threshold. The R-wave width is the difference between the onset sample point number and the offset sample point number, i.e. the number of sampling intervals between onset and offset.

For an R-wave having a negative polarity on the raw waveform, the maximum negative pulse will precede the maximum positive pulse on the fourth order difference signal. As such, the onset threshold is set as a proportion of the maximum negative peak amplitude of the maximum negative pulse of the fourth order difference signal, and the offset threshold is set as a proportion of the maximum positive peak amplitude of the maximum positive pulse. The R-wave onset is detected as the first sample point to cross the onset threshold when moving left (earlier in time) from the maximum negative peak. The R-wave offset is detected as the first sample point to cross the offset threshold moving right (later in time) from the maximum positive peak. The R-wave width is the difference between the onset sample point and the offset sample point. This method of computing an R-wave width based on onset and offset points identified from the fourth order difference signal is illustrated below in FIG. 14.

The device sets a morphology analysis window in response to the R-wave width determined from the fourth order difference signal, Block 824. The morphology of the R-wave itself is of greatest interest in classifying the unknown beat. Processing time can be reduced by comparing only the sample points of greatest interest without comparing extra points, for example baseline points or Q- or S-wave points, preceding or following the R-wave. The morphology analysis window is therefore a proportion of the sample points that is less than the total number of sample points aligned in the alignment window.

In one embodiment, different ranges of R-wave width measurements may be defined for which different respective sample numbers will be used to set the morphology analysis window. For example, if the R-wave width is greater than 30 sample intervals, the morphology analysis window is set to a first number of sample points. If the R-wave width is greater than 20 sample intervals but less than or equal to 30 sample intervals, the morphology analysis window is set to a second number of sample points less than the first number of sample points. If the R-wave width is less than or equal to 20 sample points, the morphology analysis window is set to a third number of sample points less than the second number of sample points. Two or more R-wave width ranges may be defined, each with a corresponding number of sample points defining the morphology analysis window. At least one of the R-wave width ranges is assigned a number of sample points defining the morphology analysis window to be less than the alignment window. In some embodiments all of the R-wave width ranges are assigned a number of sample points defining the morphology analysis window to be less than the alignment window.

In the example given above, the alignment window is 53 sample points. If the R-wave width is greater than 30 sample intervals, the morphology window is defined to be 48 sample points. The morphology analysis window may include 23 points preceding the R-wave sense point, the R-wave sense point itself, and 24 points after the R-wave sense point. If the R-wave width is greater than 20 but less than or equal to 30 sample intervals, the morphology window is defined to be 40 sample points (e.g. 19 before the R-wave sense point and 20 after the R-wave sense signal). If the R-wave width is less than or equal to 20 sample intervals, the window is defined to be 30 sample points (e.g. 14 before and 15 points after the R-wave sense point and including the R-wave sense point).

In other embodiments, the number of sample points in the morphology analysis window may be defined as a fixed number of sample points greater than the R-wave width, for example the R-wave width plus 12 sample points. In another example, the number of sample points defining the morphology analysis window may be computed as the R-wave width plus a rounded or truncated percentage of the R-wave width. For example, the morphology analysis window may be defined as the R-wave width plus fifty percent of the R-wave width (i.e. 150% of the R-wave width), up to a maximum of the total alignment window or some portion less than the total alignment window.

The morphology window is applied to both the unknown beat and the template. With the template and unknown cardiac signal aligned within the alignment window, the same number of sample points taken prior to and after the unknown beat alignment point is taken prior to and after the template alignment point.

After setting the morphology analysis window, Block 824, a morphology metric of the similarity between the unknown signal and the template, such as the normalized waveform area difference (NWAD), for example, is computed, Block 826. Different methods may be used to compute a NWAD. In an illustrative method, the NWAD is computed by normalizing the absolute amplitude of each of the unknown beat sample points and the template sample points within the morphology window by a respective absolute maximum peak amplitude value. A waveform area difference is then calculated by summing the absolute amplitude differences between each aligned pair of normalized sample points in the unknown signal and in the template over the morphology window.

This waveform area difference may be normalized by a template area. The template area is computed as the sum of all of the absolute values of the normalized template sample points in the morphology window. The NWAD is then calculated as the ratio of the waveform area difference to the template area. The NWAD for the aligned signals is stored.

This NWAD may be compared to a threshold to classify the unknown beat as matching the template based on a high correlation between the unknown beat and the template evidenced by a NWAD exceeding a match threshold. One or more NWADs may be computed for a given unknown beat. In the example shown in FIG. 12, additional NWADs may be computed by shifting the aligned template relative to the already aligned unknown signal by one or more sample points, Block 828. In one embodiment, the template is shifted by one sample point to the right, two sample points to the right, one sample point to the left and two sample points to the left to obtain five different alignments of the template and unknown signal. For each template alignment, i.e. with alignment points aligned, and with template and unknown signal alignment points shifted relative to each other by one point and two points in each direction, a NWAD is computed, Block

830. In this way, five NWADs are computed to measure the similarity between the unknown beat and the template (in aligned and shifted positions).

The device selects the NWAD having the greatest value as the morphology metric for the unknown beat, which is then compared to the match threshold, Block 832, to classify the unknown beat as being either a match beat or a non-match, Block 834, as described above in Blocks 724-728 of FIG. 10.

Figure 13:
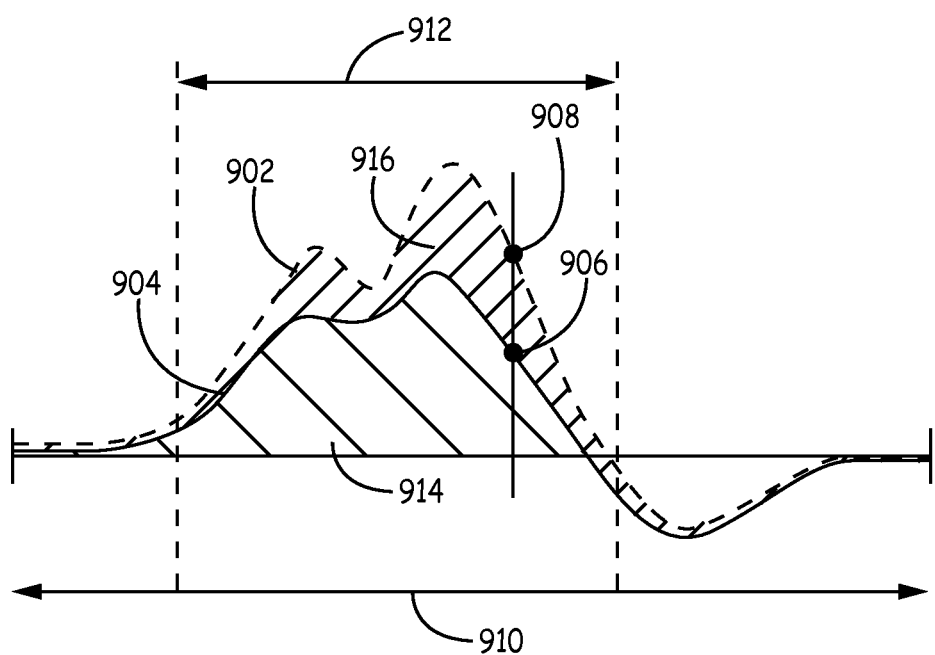
FIG. 13 is an exemplary plot of alignment of an unknown beat and a template for computing a normalized waveform area difference during beat-based analysis, according to one embodiment.

FIG. 13 is an exemplary plot of alignment of an unknown beat and a template for computing a normalized waveform area difference during beat-based analysis, according to one embodiment. As illustrated in FIG. 13, the unknown raw ECG signal 902 and the raw ECG signal template 904 (ensemble average of n raw signals aligned using fourth order difference signal) are used for determining a morphology match metric over a morphology analysis window 912. The width of the morphology analysis window 912 and the alignment of the unknown signal 902 and template 904 are based on analysis of fourth order difference.

The raw ECG signal 902 is aligned with a template alignment point 906 of the template 904 of the raw ECG signal established during NSR, identified from an ensemble averaged fourth order difference signal as the maximum absolute pulse amplitude value. An unknown signal alignment point 908 is identified from the fourth order difference signal of the unknown raw ECG signal 902. The unknown signal alignment point 908 is the maximum absolute pulse amplitude value having the same polarity as the template alignment point 906.

After aligning the template 904 with the unknown raw ECG signal 902 over an alignment window 910, a morphology window 912 is set. The morphology window 912 is a subset of, i.e. shorter than or fewer sample points than, the alignment window 910. The morphology window 912 is set based on an R-wave width measured from the fourth order difference signal of the unknown signal as described below in conjunction with FIG. 14. The morphology analysis window 912 is set in response to the R-wave width measurement as some sample number greater than the R-wave width, as described above.

The device determines a template area 914 as the sum of all of the normalized absolute values of the template sample points within the morphology analysis window 912. The values are normalized by the absolute value of the maximum amplitude of the template. The waveform area difference 916 is computed as the summation of the absolute values of the differences between the aligned normalized absolute values of the unknown ECG signal sample points and the normalized absolute values of the template sample points. The NWAD is determined by taking the ratio of the waveform area difference 916 to the template area 914, which is then used in the determination, Block 724, of whether the unknown beat is a match beat, Block 726, or a non-match beat, Block 728, in FIG. 10.

Figure 14:
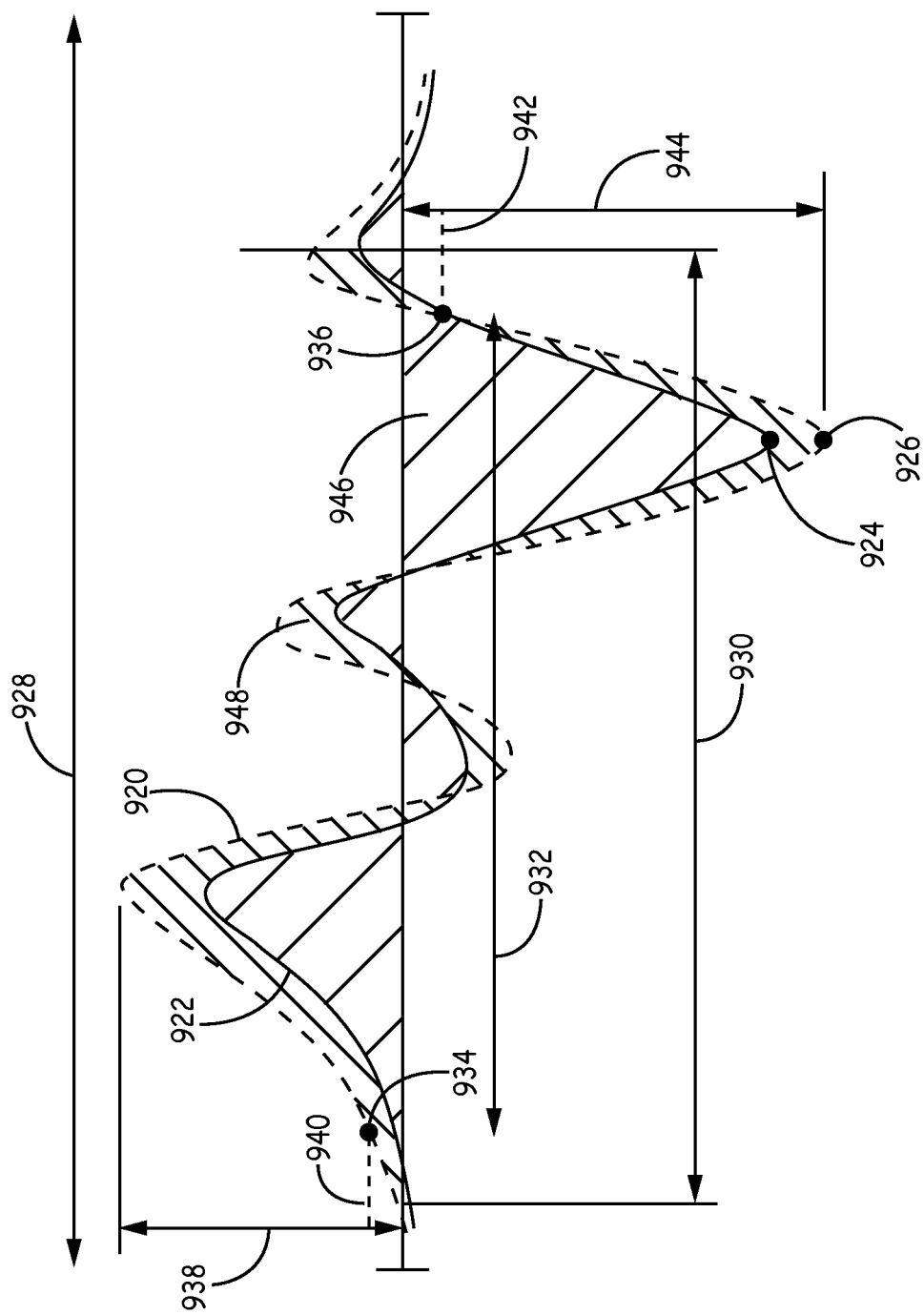
FIG. 14 is an exemplary plot illustrating a technique for determining an R-wave width and computing a normalized waveform area difference during beat-based analysis, according to another embodiment.

FIG. 14 is an exemplary plot illustrating a technique for determining an R-wave width and computing a normalized waveform area difference during beat-based analysis, according to another embodiment. In the example illustrated in FIG. 14, a fourth order difference signal 920 of the unknown raw ECG signal is aligned with a fourth order difference signal template 922 for determining a morphology match metric over a morphology analysis window 930.

The unknown fourth order difference signal 920 is derived from the unknown raw ECG signal sensed by the device and is aligned with the fourth order difference template 922 established during NSR. The template alignment point 924 is identified as the maximum absolute pulse amplitude value of the fourth order difference template. The unknown signal alignment point 926 is identified as the maximum absolute pulse amplitude value having the same polarity as the template alignment point 924. The unknown fourth order difference signal 920 is shifted over the alignment window 928 by an alignment shift required to align the unknown signal alignment point 926 with the template alignment point 924 as shown.

After aligning the template 922 with the unknown fourth order difference signal 920 over alignment window 928, a morphology window 930 is set. The morphology window 930 is a subset of the alignment window 928 and is based on an R-wave width 932 measured from the unknown fourth order difference signal 920.

In order to determine the R-wave width 932, the device determines the difference between an R-wave onset point 934 and an R-wave offset point 936 of the fourth order difference signal 920 of the unknown beat. In order to determine an R-wave onset point 934, the device determines a maximum positive pulse peak amplitude 938, and sets an onset threshold 940 as a proportion of the maximum positive pulse peak amplitude 938. In one embodiment, the device sets the onset threshold 940 as one-eighth of the maximum positive pulse peak amplitude 938. The onset point 934 is identified as the first point to the left of the maximum positive pulse peak crossing the onset threshold 940, i.e. equal to or greater than the onset threshold 940.

The device sets an offset threshold 942 as a proportion of a maximum negative pulse peak amplitude 944, and the offset point 936 is identified as the first point crossing the offset threshold 942 to the right of the maximum negative pulse. The device determines the R-wave width 932 as being the difference between the onset point 934 and the offset point 936. The morphology analysis window 930 is set in response to the R-wave width measurement as some sample number greater than the R-wave width 932, as described previously.

In other examples, the maximum negative pulse may occur earlier in the alignment window than the maximum positive pulse. If this is the case, the onset threshold is set as a proportion of the maximum negative pulse peak amplitude and the onset point is determined as the first point crossing the onset threshold to the left of the maximum negative peak. Likewise, the offset threshold is set as a proportion of the maximum positive pulse peak amplitude, and the offset point is determined as the first point to the right of the maximum positive pulse to cross the offset threshold.

The morphology analysis window 930 may be centered on an R-wave sense signal. In some embodiments, the morphology analysis window 930, determined from the fourth order difference signal 920, is applied to the unknown raw ECG signal aligned with a raw ECG signal template, for example analysis window 912 as shown in FIG. 13. The morphology match metric is determined from the raw ECG signal 902 and template 904. In the example illustrated in FIG. 14, the morphology analysis window 930 is applied to the fourth order difference signal 920; the morphology match metric is determined from the fourth order difference signal 920 and fourth order difference template 922.

The template area 946 is computed as the sum of all of the normalized absolute values of the template sample points within the morphology window 930. The values are normalized by the absolute value of the maximum amplitude of the template 922 (in this example point 926). The device determines the waveform area difference 948 as the summation of the absolute differences between the aligned normalized absolute values of the unknown fourth order difference signal sample points and the normalized absolute values of the template sample points. The NWAD is determined by the device as the ratio of the waveform area difference 948 and the template area 946, and is compared to a match threshold to classify the unknown beat corresponding to the fourth order difference signal 920 as being either a match beat or a non-match beat, Blocks 726 and 728 of FIG. 10.

Returning to FIG. 10, once the individual beat is identified as being either a match beat, Block 726, or a non-match beat, Block 728, using the normalized waveform area difference analysis described above, the device determines whether the individual beat may be corrupted, such as by noise, for example, thereby reducing the level of confidence in the determination that the beat is either a match beat, Block 726, or a non-match beat, Block 728. Based on the determined level of confidence, the device may determine that the beat should be discarded in the beat-based shockable/not shockable analysis for the three-second window, as described below.

If the beat confidence threshold is satisfied, Yes in Block 730, the beat is considered a high confidence beat and therefore is identified as a beat that should not be discarded, Block 732. If the beat confidence threshold is not satisfied, No in Block 730, the beat is considered a low confidence beat and therefore is identified as a beat that should be discarded, Block 734. Once the beat is identified as either being a high confidence beat, Block 732, or a low confidence beat, Block 734, the device determines whether the determination has been made for all of the beats in the three-second window, Block 736. If the determination has not been made for all of the beats in the three-second window, the process of identifying a beat as being either a match beat or a non-match beat and a high confidence beat or a low confidence beat, Blocks 720-734, is repeated for the next beat.

Figure 15:
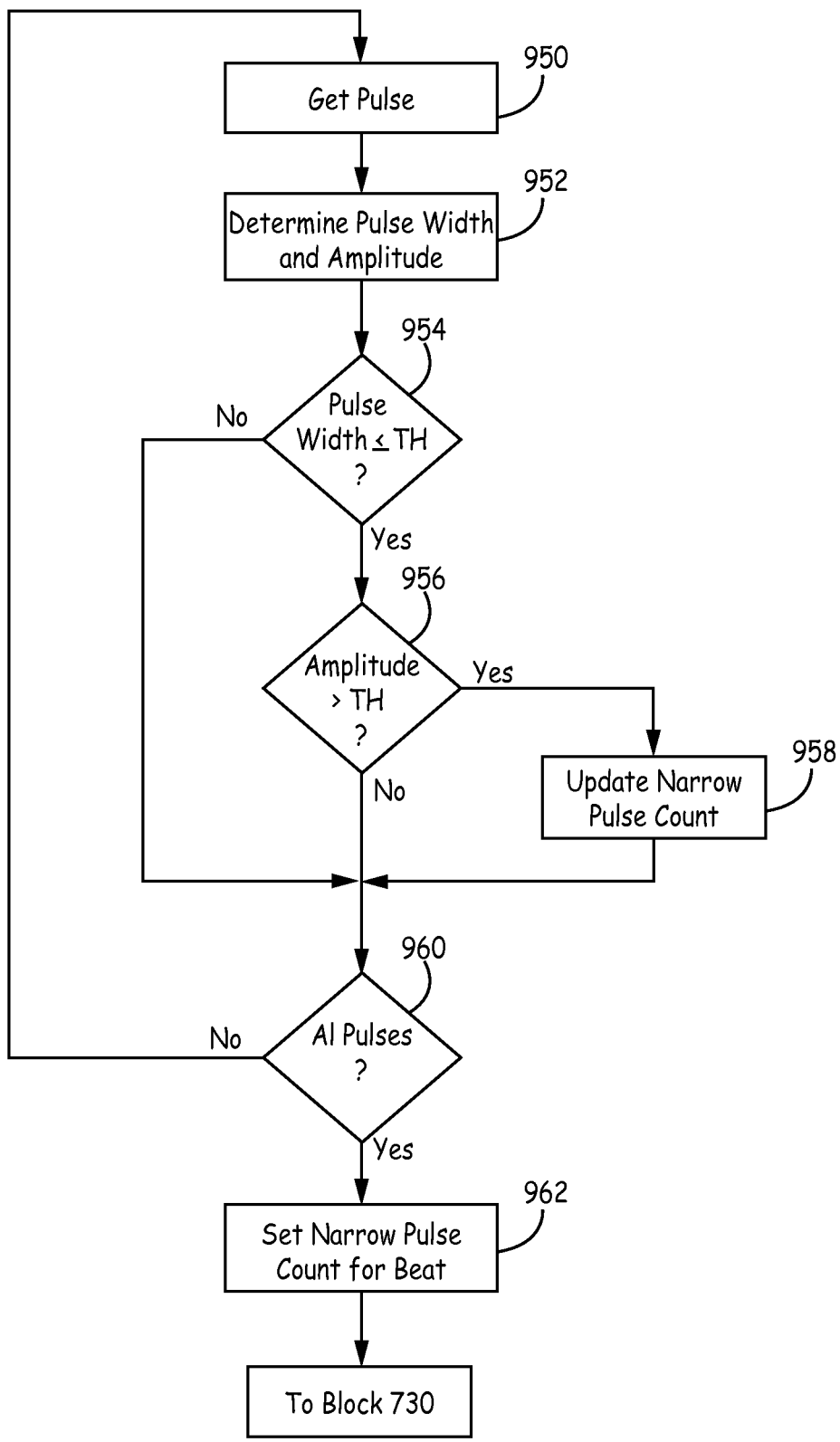
FIG. 15 is a flowchart of a method for determining an individual beat confidence during beat-based analysis, according to one embodiment.

FIG. 15 is a flowchart of a method for determining an individual beat confidence during beat-based analysis, according to one embodiment. In order to determine whether the beat confidence threshold is satisfied in Block 730 of FIG. 10, the device determines a narrow pulse count, i.e., pulse number, for the plurality of pulses associated with the beat using parameters previously determined during the normalized waveform area difference analysis in Block 722, described above.

For example, in order to determine the narrow pulse count for each individual beat, the device determines, for each individual pulse of the pulses identified in the alignment window for the beat during the alignment of the unknown beat with the template, Block 810 of FIG. 11, whether the width of the pulse is less than a predetermined threshold. In particular, as illustrated in FIG. 15, the device gets a single pulse of the identified pulses for the beat, Block 950, determines a pulse width associated with the pulse, Block 952, and determines whether the pulse width is less than or equal to a pulse width threshold, Block 954.

In addition to determining whether the pulse width of the individual pulse is less than or equal to the pulse width threshold, Yes in Block 954, the device also determines whether the absolute amplitude of the pulse is greater than an amplitude threshold, Block 956. According to an embodiment, the pulse width threshold may be set as 23 milliseconds, for example, and the amplitude threshold is set as a fraction, such as one eighth, for example, of the maximum slope used in the determination of whether the slope threshold was met during the aligning of the beat with the template, Block 808 of FIG. 11.

While the pulse width determination, Block 954, is illustrated as occurring prior to the amplitude threshold determination, Block 956, it is understood that the sequence of the determinations of Blocks 954 and 956 is not overriding.

Therefore, if either the pulse width of the individual pulse is not less than or equal to the pulse width threshold, No in Block 954, or the absolute amplitude of the pulse is not greater than the amplitude threshold, No in Block 956, the pulse is determined not to be included in the narrow pulse count. The device continues by determining whether the determination of whether the number of pulses satisfying the narrow pulse count parameters has been made for all of the identified pulses (Block 810 of FIG. 11) for the beat, Block 960. If the determination has not been made for all of the identified pulses, No in Block 960, the device identifies the next pulse, Block 950, and the process of determining a narrow pulse count for that beat, Blocks 952-958, is repeated for the next pulse.

If both the pulse width of the individual pulse is less than or equal to the pulse width threshold, Yes in Block 954, and the absolute amplitude of the pulse is greater than the amplitude threshold, Yes in Block 956, the number of pulses satisfying the width and amplitude thresholds for the individual beat, i.e., the narrow pulse count, is increased by one, Block 958.

Once the determination has been made for all of the identified pulses associated with the beat, Yes in Block 960, the device sets the narrow pulse count for the beat, Block 962, equal to the resulting updated narrow pulse count, Block 958. In this way, the narrow pulse count for the beat is the total number of pulses of the identified pulses for the beat that satisfy both the width threshold, i.e., the number of pulses that have a pulse width less than 23 milliseconds, and the amplitude threshold, i.e., the number of pulses that have an absolute amplitude greater than one eighth of the maximum slope used in the determination of whether the slope threshold was met during the aligning of the beat with the template, Block 808 of FIG. 11. The final narrow pulse count from Block 962 is then used by the device in the determination of whether the beat confidence threshold is satisfied for the beat, Block 730 of FIG. 10.

Returning to FIG. 10, when determining whether the beat confidence threshold has been satisfied for the beat, the device determines compares the narrow pulse count for the beat obtained from Block 962 of FIG. 15 to a narrow pulse count threshold, such as 5, for example. If the narrow pulse count is less than the narrow pulse count threshold, the beat confidence threshold is satisfied, Yes in Block 730, the beat is considered a high confidence beat and therefore is identified as a beat that should not be discarded, Block 732. If the narrow pulse count is not less than the narrow pulse count threshold, the beat confidence threshold is not satisfied, No in Block 730, the beat is considered a low confidence beat and therefore is identified as a beat that should be discarded, Block 734.

Once the determination of the beat being either a match beat or a non-match beat, and either a high confidence or a low confidence beat has been made for all of the beats in the three-second window, Yes in Block 736, a determination is made as to whether the number of non-match beats in the three-second window that are also high confidence beats is greater than a non-match threshold, Block 738. According to an embodiment of the disclosure, the non-match threshold is set as a predetermined percentage, such as 75 percent for example, so that if the number of individual beats in the three-second window that are identified as being non-match beats is greater than 75 percent of the number of all of the beats in the window, Yes in Block 738, the three-second window is identified as being shockable based on the beat-based analysis, Block 740.

On the other hand, if the number of individual beats in the three-second window that are identified as being both non-match beats and high confidence beats is not greater than 75 percent of the number of all of the beats in the window, No in Block 738, the three-second window is identified as being not shockable based on the beat based analysis, Block 742. The beat-based analysis determination of the three-second windows as being shockable 740 or not shockable, Block 742 is then used in combination with the waveform morphology analysis of both of the three-second windows being shockable, Blocks 353, 357, 363 and 369 or both not shockable, Blocks 351, 355, 359, 365 and 367 to determine whether to transition to the next state, Block 370, as described above.

Figure 16:
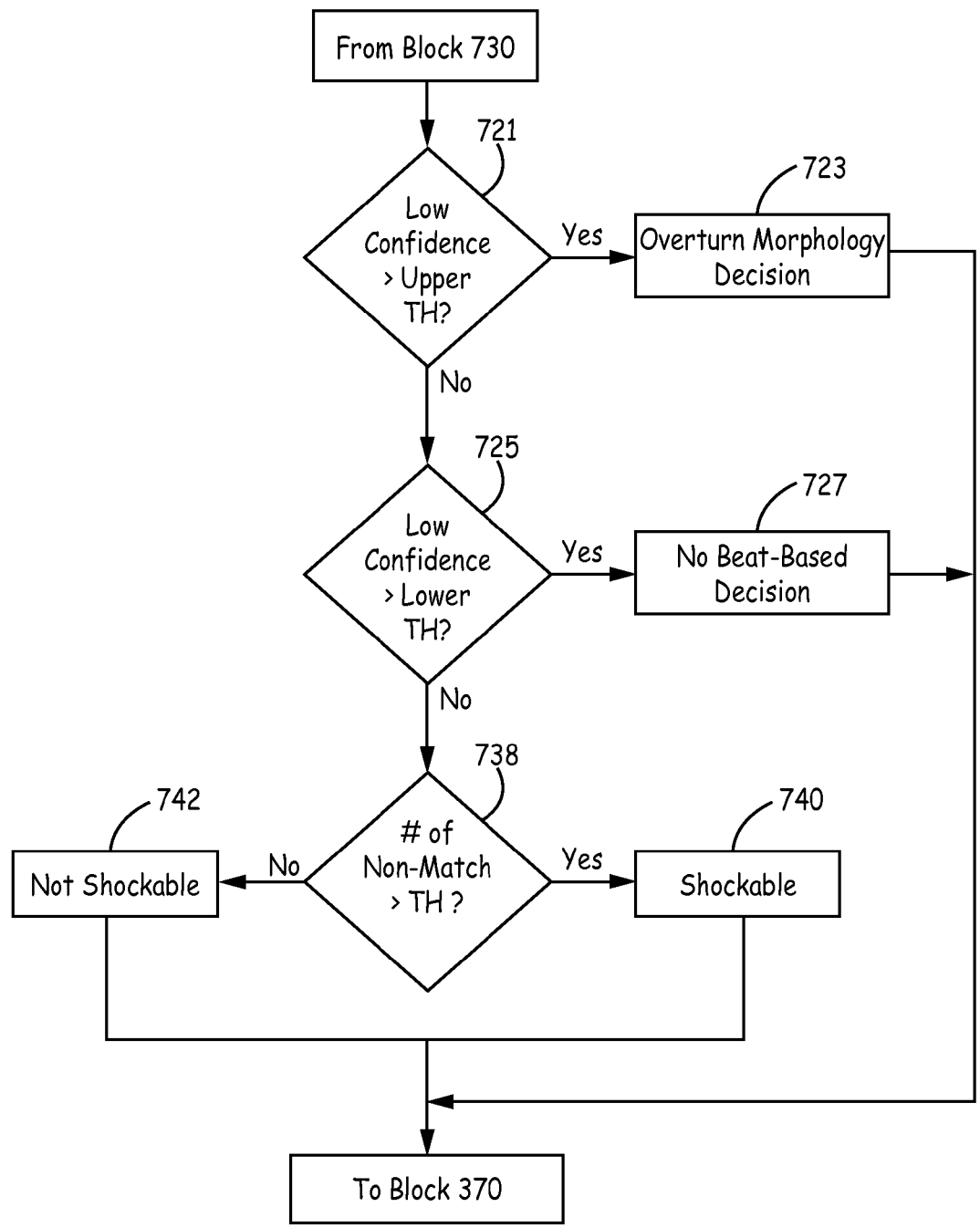
FIG. 16 is a flowchart of a method for performing beat-based analysis during detection of arrhythmias in a medical device, according to an embodiment of the present disclosure.

FIG. 16 is a flowchart of a method for performing beat-based analysis during detection of arrhythmias in a medical device, according to an embodiment of the present disclosure. As illustrated in FIGS. 10 and 16, according to another embodiment, once the determination of whether both the beat is identified as being either a match beat, Block 726, or a non-match beat, Block 728, and as being either a high confidence beat, Block 732, or a low confidence beat, Block 734, has been made for all of the beats in the three-second window, Yes in Block 736, the device may also further distinguish the information used to determine whether to transition between states in Block 732 of FIG. 4. For example, as illustrated in FIG. 16, the device determines whether a predetermined number of the total number of beats within the three-second window are greater than an upper low confidence threshold, Block 721, that would indicate a likelihood that the beat-based analysis may be corrupted to a level high enough that both the gross morphology and the beat-based determinations of shockable or not shockable for the window should be ignored. In one embodiment, the upper low confidence threshold is set as a predetermined percentage, such as two-thirds, for example, so that if the number of beats in the window that are identified as being low confidence for the three-second window is greater than two-thirds of the total number of beats in the window, Yes in Block 721, both the beat-based decision of shockable, Block 740 or not shockable, Block 742, and the gross morphology-based decision of shockable used in the decision as to whether to transition between states in Block 372 is overridden.

In addition, the device may also determine whether a predetermined number of the total number of beats within the three-second window are greater than a lower low confidence threshold, Block 725, that would indicate a likelihood that the beat-based analysis may be corrupted and therefore should be ignored. In one embodiment, the lower low confidence threshold is set as a predetermined percentage, less than the upper low confidence threshold, such as one-third, for example, so that if the number of beats in the window that are identified as being low confidence for the three-second window is greater than one third (but less than two-thirds) of the total number of beats in the window, Yes in Block 725, the beat-based decision of shockable 740 or not shockable 742 are ignored, Block 727, so that the decision as to whether to transition between states in Block 372 is made using only the gross morphology-based analysis for that window.

On the other hand, if both the number of beats in the window that are identified as being low confidence for the three-second window is not greater than two-thirds of the total number of beats in the window, No in Block 721, and the number of beats in the window that are identified as being low confidence for the three-second window is not greater than one third (but less than two-thirds) of the total number of beats in the window, No in Block 725, the device determines whether the number of non-match beats in the three-second window that are also high confidence beats is greater than a non-match threshold, Block 738, is made using both the beat-based and the gross morphology based analysis, as described above in reference to FIG. 10. As a result, the decision as to whether to transition between states in Block 372 is made using both the gross morphology-based analysis and the beat-based analysis for that three-second window.

Figure 17:
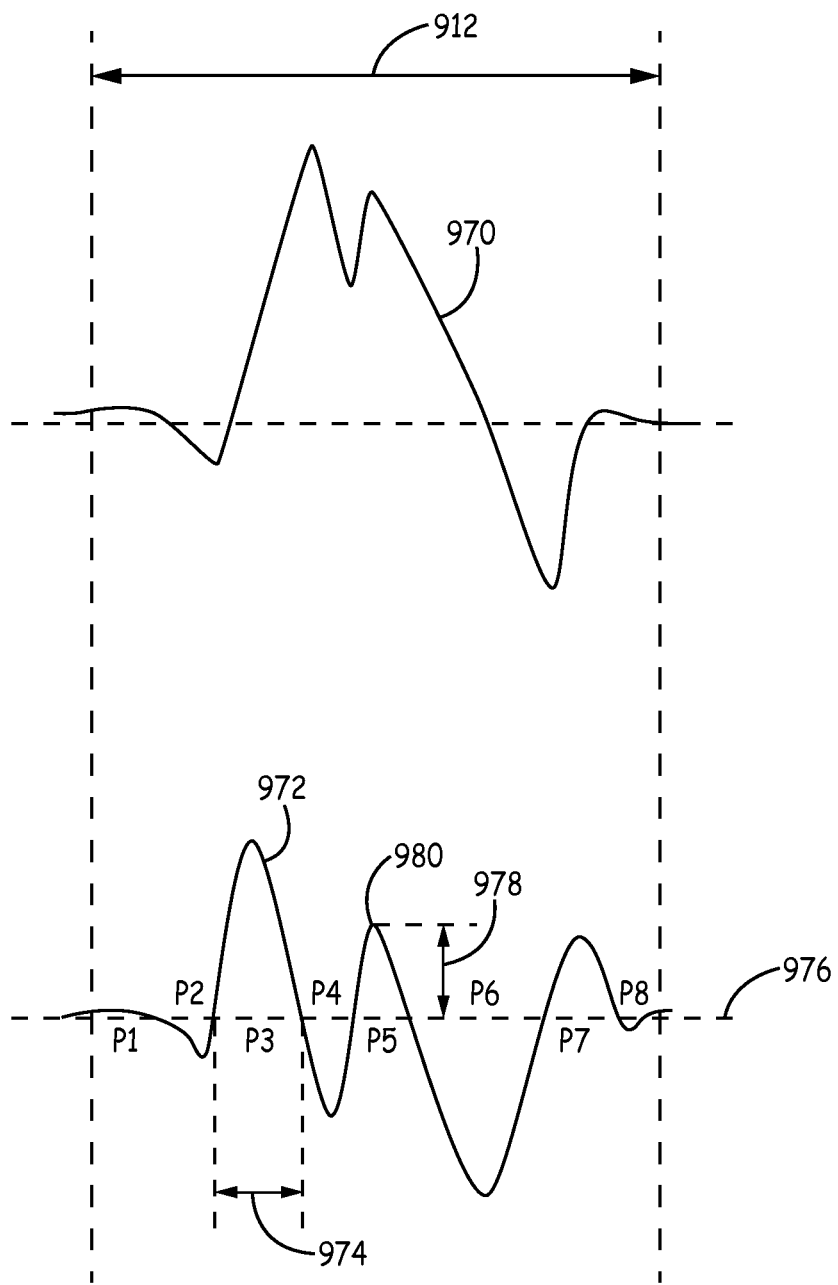
FIG. 17 is an exemplary plot illustrating determining pulses for a beat within a window during a beat-based analysis according to an embodiment of the disclosure.

FIG. 17 is an exemplary plot illustrating determining pulses for a beat within a window during a beat-based analysis according to an embodiment of the disclosure. As illustrated in FIG. 17, the device senses each individual R-wave 970 occurring within a three-second window, determines a morphology window 912, and determines a number of pulses, i.e., pulse count, associated with the R-wave 970 from the fourth order difference of the R-wave 972 within the morphology window 912 for use in determining a beat confidence for the R-wave 970, as described above. For example, in response to the fourth order difference 972 of the sensed R-wave 970, the device determines there are eight pulses P1-P8 associated with the R-wave 970. Pulses P1, P3, P5 and P7 are positive pulses and P2, P4, P6 and P8 are negative pulses, with each pulse P1-P8 having a pulse width 974 define by zero-crossings of the pulses with a baseline 976, and a pulse amplitude 978 defined between a pulse peak 980 and the baseline 976. In this way, the device uses the determined pulses P1-P8 and their associated pulse width 974 and pulse amplitude 978 to determine a narrow pulse count, as described above.

Thus, a method and apparatus for verifying discriminating of a cardiac event have been presented in the foregoing description with reference to specific embodiments. It is appreciated that various modifications to the referenced embodiments may be made without departing from the scope of the disclosure as set forth in the following claims.

I claim:

1. A method of detecting a cardiac event in a medical device, comprising:
    sensing cardiac signals from a plurality of electrodes, the plurality of electrodes forming a first sensing vector sensing a first interval of the cardiac signal comprising a plurality of beats during a predetermined time period and a second sensing vector simultaneously sensing a second interval of the cardiac signal comprising a plurality of beats during the predetermined time period;
    determining, for each of the first interval and the second interval, whether each beat of the plurality of beats is one of a match beat and a non-match beat;
    determining whether each beat of the plurality of beats is one of a high confidence beat and a low confidence beat;
    determining, for each of the first interval and the second interval, the number of beats determined to be both a non-match beat and a high confidence beat is greater than a non-match threshold;
    identifying each of the first interval and the second interval as being one of shockable and not shockable in response to the number of beats identified as being both a non-match beat and a high confidence beat; and
    determining whether to deliver therapy for the cardiac event in response to identifying of each of the first interval and the second interval as being one of shockable and not shockable.

2. The method of claim 1, wherein determining whether each beat of the plurality of beats is one of a match beat and a non-match beat comprises:
    determining a fourth order difference signal corresponding to the beat;
    determining a template alignment point and a beat alignment point in response to the fourth order difference signal;

aligning the template and the beat in response to the template alignment point and the beat alignment point; and
determining a morphology match metric between the aligned template and the beat.

3. The method of claim 2, wherein determining whether each beat of the plurality of beats is one of a high confidence beat and a low confidence beat comprises:
   determining a number of pulses associated with the beat being less than a narrow pulse threshold; and
   comparing the number of pulses associated with the beat being less than a narrow pulse threshold to a narrow pulse count threshold.

4. The method of claim 3, wherein determining a number of pulses associated with the beat being less than a narrow pulse threshold comprises determining, for each pulse associated with a beat, whether both a pulse width is less than a pulse width threshold and a pulse amplitude is greater than a pulse amplitude threshold.

5. The method of claim 2, wherein determining whether each beat of the plurality of beats is one of a match beat and a non-match beat comprises:
   comparing a slope of the fourth order difference signal to a maximum slope threshold;
   determining pulses associated with the beat in response to the comparing;
   determining a pulse amplitude for each pulse; and
   determining a maximum pulse amplitude in response to the determined amplitudes.

6. The method of claim 5, wherein determining whether each beat of the plurality of beats is one of a high confidence beat and a low confidence beat comprises:
   determining, for each pulse, whether a width of the pulse is less than a narrow pulse width threshold;
   determining, for each pulse, whether the determined pulse amplitude is greater than a pulse amplitude threshold;
   determining a number of the determined pulses that are both less than the narrow pulse threshold and greater than the pulse amplitude threshold; and
   determining whether the number of the determined pulses that are both less than the narrow pulse threshold and greater than the pulse amplitude threshold is greater than a beat confidence threshold.

7. The method of claim 6, wherein the pulse width threshold is approximately 23 milliseconds, the pulse amplitude threshold is equal to a fraction of the slope of the fourth order difference signal, and the beat confidence threshold is five beats.

8. The method of claim 6, further comprising:
   identifying each of the first interval and the second interval as being one of shockable and not shockable in response to gross morphology metrics of the first interval and the second interval;
   determining whether the number of non-match beats is greater than a non-match threshold;
   identifying each of the first interval and the second interval as being one of shockable and not shockable in response determining whether the number of non-match beats is greater than a non-match threshold; and
   determining whether beats of the plurality of beats determined to be low confidence beats is greater than a first low confidence threshold, wherein the identifying each of the first interval and the second interval as being one of shockable and not shockable in response to both the gross morphology metrics and the determining whether the number of non-match beats is greater than a non-match threshold is excluded from the determination of whether to deliver therapy in response to beats of the plurality of beats determined to be low confidence beats being greater than the first low confidence threshold.

9. The method of claim 8, further comprising:
   determining whether beats of the plurality of beats determined to be low confidence beats is greater than a first low confidence threshold; and
   determining whether beats of the plurality of beats determined to be low confidence beats is greater than a second low confidence threshold less than the first low confidence threshold, wherein the determination of whether to deliver therapy is made in response to the identification of each of the first interval and the second interval as being one of shockable and not shockable only in response to the gross morphology metrics in response to beats of the plurality of beats determined to be low confidence beats not being greater than the first low confidence threshold and being greater than the second low confidence threshold.

10. The method of claim 9, wherein the determination of whether to deliver therapy is made in response to only the identification of each of the first interval and the second interval as being one of shockable and not shockable in response to both the gross morphology metrics and the determining whether the number of non-match beats is greater than a non-match threshold in response to beats of the plurality of beats determined to be low confidence beats both not being greater than the first low confidence threshold and not being greater than the second low confidence threshold.

11. A medical device for detecting a cardiac event, comprising:
   a plurality of electrodes sensing cardiac signals from a plurality of electrodes, the plurality of electrodes forming a first sensing vector sensing a first interval of the cardiac signal comprising a plurality of beats during a predetermined time period and a second sensing vector simultaneously sensing a second interval of the cardiac signal comprising a plurality of beats during the predetermined time period; and
   a processor configured to determine, for each of the first interval and the second interval, whether each beat of the plurality of beats is one of a match beat and a non-match beat, determine whether each beat of the plurality of beats is one of a high confidence beat and a low confidence beat, determine, for each of the first interval and the second interval, the number of beats determined to be both a non-match beat and a high confidence beat is greater than a non-match threshold, identify each of the first interval and the second interval as being one of shockable and not shockable in response to the number of beats identified as being both a non-match beat and a high confidence beat, and determine whether to deliver therapy for the cardiac event in response to identifying of each of the first interval and the second interval as being one of shockable and not shockable.

12. The medical device of claim 11, wherein determining whether each beat of the plurality of beats is one of a match beat and a non-match beat comprises:
   determining a fourth order difference signal corresponding to the beat;
   determining a template alignment point and a beat alignment point in response to the fourth order difference signal;
   aligning the template and the beat in response to the template alignment point and the beat alignment point; and
   determining a morphology match metric between the aligned template and the beat.

13. The medical device of claim 12, wherein determining whether each beat of the plurality of beats is one of a high confidence beat and a low confidence beat comprises:
  determining a number of pulses associated with the beat being less than a narrow pulse threshold; and
  comparing the number of pulses associated with the beat being less than a narrow pulse threshold to a narrow pulse count threshold.

14. The medical device of claim 13, wherein determining a number of pulses associated with the beat being less than a narrow pulse threshold comprises determining, for each pulse associated with a beat, whether both a pulse width is less than a pulse width threshold and a pulse amplitude is greater than a pulse amplitude threshold.

15. The medical device of claim 12, wherein determining whether each beat of the plurality of beats is one of a match beat and a non-match beat comprises:
  comparing a slope of the fourth order difference signal to a maximum slope threshold;
  determining pulses associated with the beat in response to the comparing;
  determining a pulse amplitude for each pulse; and
  determining a maximum pulse amplitude in response to the determined amplitudes.

16. The medical device of claim 15, wherein determining whether each beat of the plurality of beats is one of a high confidence beat and a low confidence beat comprises:
  determining, for each pulse, whether a width of the pulse is less than a narrow pulse width threshold;
  determining, for each pulse, whether the determined pulse amplitude is greater than a pulse amplitude threshold;
  determining a number of the determined pulses that are both less than the narrow pulse threshold and greater than the pulse amplitude threshold; and
  determining whether the number of the determined pulses that are both less than the narrow pulse threshold and greater than the pulse amplitude threshold is greater than a beat confidence threshold.

17. The medical device of claim 16, wherein the pulse width threshold is approximately 23 milliseconds, the pulse amplitude threshold is equal to a fraction of the slope of the fourth order difference signal, and the beat confidence threshold is five beats.

18. The medical device of claim 16, further comprising:
  identifying each of the first interval and the second interval as being one of shockable and not shockable in response to gross morphology metrics of the first interval and the second interval;
  determining whether the number of non-match beats is greater than a non-match threshold;
  identifying each of the first interval and the second interval as being one of shockable and not shockable in response determining whether the number of non-match beats is greater than a non-match threshold; and
  determining whether beats of the plurality of beats determined to be low confidence beats is greater than a first low confidence threshold, wherein the identifying each of the first interval and the second interval as being one of shockable and not shockable in response to both the gross morphology metrics and the determining whether the number of non-match beats is greater than a non-match threshold is excluded from the determination of whether to deliver therapy in response to beats of the plurality of beats determined to be low confidence beats being greater than the first low confidence threshold.

19. The medical device of claim 18, further comprising:
  determining whether beats of the plurality of beats determined to be low confidence beats is greater than a first low confidence threshold; and
  determining whether beats of the plurality of beats determined to be low confidence beats is greater than a second low confidence threshold less than the first low confidence threshold, wherein the determination of whether to deliver therapy is made in response to the identification of each of the first interval and the second interval as being one of shockable and not shockable only in response to the gross morphology metrics in response to beats of the plurality of beats determined to be low confidence beats not being greater than the first low confidence threshold and being greater than the second low confidence threshold.

20. The medical device of claim 19, wherein the determination of whether to deliver therapy is made in response to only the identification of each of the first interval and the second interval as being one of shockable and not shockable in response to both the gross morphology metrics and the determining whether the number of non-match beats is greater than a non-match threshold in response to beats of the plurality of beats determined to be low confidence beats both not being greater than the first low confidence threshold and not being greater than the second low confidence threshold.

21. A non-transitory, computer-readable storage medium storing instructions for causing a processor included in a medical device to perform a method for determining a cardiac event, the method comprising:
  sensing cardiac signals from a plurality of electrodes, the plurality of electrodes forming a first sensing vector sensing a first interval of the cardiac signal comprising a plurality of beats during a predetermined time period and a second sensing vector simultaneously sensing a second interval of the cardiac signal comprising a plurality of beats during the predetermined time period;
  determining, for each of the first interval and the second interval, whether each beat of the plurality of beats is one of a match beat and a non-match beat;
  determining whether each beat of the plurality of beats is one of a high confidence beat and a low confidence beat;
  determining, for each of the first interval and the second interval, the number of beats determined to be both a non-match beat and a high confidence beat is greater than a non-match threshold; and
  identifying each of the first interval and the second interval as being one of shockable and not shockable in response to the number of beats identified as being both a non-match beat and a high confidence beat; and
  determining whether to deliver therapy for the cardiac event in response to identifying of each of the first interval and the second interval as being one of shockable and not shockable.

* * * * *